US012558572B2

(12) United States Patent
Peng et al.

(10) Patent No.: US 12,558,572 B2
(45) Date of Patent: Feb. 24, 2026

(54) ULTRASONIC TREATMENT TIP AND ULTRASONIC THERAPEUTIC APPARATUS

(71) Applicant: SHENZHEN PENINSULA MEDICAL GROUP, Shenzhen (CN)

(72) Inventors: Yujia Peng, Shenzhen (CN); Yongsheng Liang, Shenzhen (CN); Yanan Li, Shenzhen (CN); Xiaobing Lei, Shenzhen (CN); Yi Ding, Shenzhen (CN)

(73) Assignee: SHENZHEN PENINSULA MEDICAL GROUP, Shenzhen (CN)

( * ) Notice: Subject to any disclaimer, the term of this patent is extended or adjusted under 35 U.S.C. 154(b) by 37 days.

(21) Appl. No.: 18/423,884

(22) Filed: Jan. 26, 2024

(65) Prior Publication Data

US 2024/0165430 A1     May 23, 2024

Related U.S. Application Data

(63) Continuation of application No. PCT/CN2023/104224, filed on Jun. 29, 2023.

(30) Foreign Application Priority Data

Sep. 16, 2022    (CN) .......................... 202211129050.0
Sep. 16, 2022    (CN) .......................... 202222468875.7
(Continued)

(51) Int. Cl.
    *A61N 7/02*        (2006.01)
    *H05K 7/20*        (2006.01)
(52) U.S. Cl.
    CPC ............. *A61N 7/02* (2013.01); *H05K 7/2039* (2013.01)

(58) Field of Classification Search
    CPC ........... A61N 7/02; A61N 7/00; H05K 7/2039
    See application file for complete search history.

(56) References Cited

U.S. PATENT DOCUMENTS 7,891,230 B2 *  2/2011  Randall ................... G01M 3/40
                                                        73/1.82
2004/0073118 A1 *  4/2004  Peszynski ................ A61B 8/12
                                                        600/459
(Continued)

FOREIGN PATENT DOCUMENTS

CN          101322869 A     12/2008
CN          102068283 A      5/2011
                (Continued)

OTHER PUBLICATIONS

KR-101394214-B1 Translation (Year: 2014).*
International Search Report and Written Opinion issued in corresponding PCT Application No. PCT/CN2023/104224, dated Oct. 11, 2023.

*Primary Examiner* — Adil Partap S Virk
(74) *Attorney, Agent, or Firm* — Westbridge IP LLC

(57)        ABSTRACT

Disclosed are an ultrasonic treatment tip and an ultrasonic therapeutic apparatus. The ultrasonic treatment tip is configured to connect the ultrasonic therapeutic apparatus, the ultrasonic treatment tip includes: an outer shell, a cover body, an inner shell, a heat dissipation structure, a sound-permeable membrane and a transducer, the outer shell is provided with a first port; the cover body covers the first port, the cover body and the outer shell are configured to limit an installation cavity, the cover body is provided with an avoidance hole connected to the installation cavity, and the cover body is connected to the ultrasonic treatment handle; the inner shell is provided at the installation cavity, the inner shell is provided with a receiving cavity for receiving an ultrasonic transmission medium, and the receiving cavity is provided with a second port.

10 Claims, 26 Drawing Sheets

(30)        Foreign Application Priority Data

Sep. 16, 2022   (CN) .......................... 202222468981.5
Sep. 16, 2022   (CN) .......................... 202222468985.3

(56)              References Cited

U.S. PATENT DOCUMENTS

| | | | | |
|---|---|---|---|---|
| 2008/0194961 A1* | 8/2008 | Randall | ............... | G01S 7/52017 |
| | | | | 600/459 |
| 2009/0240310 A1* | 9/2009 | Kennedy | .............. | A61N 5/0616 |
| | | | | 607/88 |
| 2011/0077557 A1* | 3/2011 | Wing | ..................... | A61B 8/546 |
| | | | | 601/2 |
| 2011/0230794 A1* | 9/2011 | van Groningen | ...... | A61B 8/546 |
| | | | | 601/2 |
| 2018/0287465 A1* | 10/2018 | Lin | ......................... | H02K 33/16 |
| 2020/0297324 A1* | 9/2020 | Song | .................. | G01S 15/8918 |
| 2021/0236859 A1* | 8/2021 | Park | ......................... | A61N 7/00 |

FOREIGN PATENT DOCUMENTS

| | | | | | |
|---|---|---|---|---|---|
| CN | 216603842 | U | | 5/2022 | |
| CN | 115531750 | A | | 12/2022 | |
| CN | 219001795 | U | | 5/2023 | |
| CN | 219001796 | U | | 5/2023 | |
| CN | 219001797 | U | | 5/2023 | |
| KR | 101394214 | B1 | * | 5/2014 | ............... A61N 7/00 |

* cited by examiner

100

100

300

500   700   800   930   600   940   400   920

610   410

700

710   730   711

712

700

510

700

31

711

510

512 513 511

63

633

632                                                631

42

100

ULTRASONIC TREATMENT TIP AND ULTRASONIC THERAPEUTIC APPARATUS

CROSS-REFERENCE TO RELATED APPLICATIONS

This application is a continuation application of International Application No. PCT/CN2023/104224, filed on Jun. 29, 2023, which claims priority to Chinese Patent Application No. 202222468981.5, filed on Sep. 16, 2022, Chinese Patent Application No. 202222468985.3, filed on Sep. 16, 2022, Chinese Patent Application No. 202222468875.7, filed on Sep. 16, 2022, and Chinese Patent Application No. 202211129050.0, filed on Sep. 16, 2022. The disclosures of the above-mentioned applications are incorporated herein by reference in their entireties.

TECHNICAL FIELD

The present application relates to the technical field of ultrasound therapy, and in particular to an ultrasonic treatment tip and an ultrasonic therapeutic apparatus.

BACKGROUND

Ultrasonic therapeutic apparatus includes an ultrasonic treatment tip, the ultrasonic treatment tip is equipped with a transducer. By converting electrical energy into sound energy, the transducer can emit ultrasonic waves toward the sound-permeable membrane to transmit the ultrasonic waves to the human body. The transducer will generate heat when working, which causes the temperature inside the ultrasonic treatment tip to be relatively high, thereby resulting in a relatively high pressure inside the ultrasonic treatment tip, which can easily cause the sound-permeable membrane to burst.

SUMMARY

The main purpose of the present application is to provide an ultrasonic treatment tip, aiming to reduce the temperature inside the ultrasonic treatment tip, thus making the pressure inside the ultrasonic treatment tip relatively low and reducing the possibility of the sound-permeable membrane bursting.

In order to achieve the above purpose, in the first aspect, the ultrasonic treatment tip proposed by the present application is configured to connect an ultrasonic treatment handle, and the ultrasonic treatment tip includes:

an outer shell provided with a first port;

a cover body covering the first port, the cover body and the outer shell are configured to limit an installation cavity, the cover body is provided with an avoidance hole connected to the installation cavity, and the cover body is connected to the ultrasonic treatment handle;

an inner shell provided at the installation cavity, the inner shell is provided with a receiving cavity for receiving an ultrasonic transmission medium, and the receiving cavity is provided with a second port;

a heat dissipation structure including a heat dissipation main body provided at the second port and a first heat dissipation convex portion passed through the avoidance hole, the first heat dissipation convex portion is connected to the heat dissipation main body;

a sound-permeable membrane, the ultrasonic treatment tip is provided with a sound-permeable opening passed through the outer shell and the inner shell, and the sound-permeable membrane is provided at the sound-permeable opening; and a transducer received at the receiving cavity, the transducer is provided with a vibrating sound-emitting surface provided toward the sound-permeable membrane.

In an embodiment, the heat dissipation structure further includes a second heat dissipation convex portion provided at the receiving cavity.

In an embodiment, the ultrasonic treatment tip further includes the ultrasonic transmission medium received at the receiving cavity, and the second heat dissipation convex portion is immersed into the ultrasonic transmission medium.

In an embodiment, a plurality of the second heat dissipation convex portions are provided.

In an embodiment, the heat dissipation main body is configured to cover the second port, the heat dissipation main body is provided with a wire via hole for a wire harness of the transducer to pass through, and the ultrasonic treatment tip further includes a first plugging element provided between the wire via hole and the wire harness of the transducer.

In an embodiment, the heat dissipation main body is provided with a via hole for ultrasonic transmission medium, and the ultrasonic treatment tip further includes a second plugging element provided at the via hole for ultrasonic transmission medium.

In an embodiment, the heat dissipation main body is provided with an avoidance area, part of the avoidance area is exposed at the cover body, the cover body is provided with a wire via hole for a wire harness of the transducer to pass through, the ultrasonic treatment tip further includes a first plugging element provided between the wire via hole and the wire harness of the transducer, and the wire via hole is exposed at the avoidance area; and/or, the cover body is provided with a via hole for ultrasonic transmission medium, the ultrasonic treatment tip further includes a second plugging element provided at the via hole for ultrasonic transmission medium, and the via hole for ultrasonic transmission medium is exposed at the avoidance area.

In an embodiment, the vibrating sound-emitting surface is provided to be a spherical arc surface or a tile surface.

In an embodiment, the sound-permeable membrane is sandwiched between the outer shell and the inner shell.

In an embodiment, the ultrasonic treatment tip further includes a transducer bracket provided at the heat dissipation main body, and the transducer is provided at the transducer bracket.

In an embodiment, a sealing ring is provided between the inner shell and the heat dissipation main body.

In the second aspect, the present application further provides an ultrasonic treatment tip, including:

a shell provided with a receiving cavity, the shell is provided with a heat dissipation structure;

a transducer module provided at the receiving cavity; and a transmission mechanism rotatably passing through the shell, the transmission mechanism is provided with a first end and a second end, the first end is transmission connected to the transducer module, the second end is configured to drivingly connected to a driving member, and the transmission mechanism is configured to drive the transducer module to perform reciprocating motion.

In an embodiment, the shell includes a shell body provided with a first port and the heat dissipation structure covering the first port, the shell body and the heat dissipation structure are configured to limit the receiving cavity, and the transmission mechanism is passed through the heat dissipation structure.

In an embodiment, the heat dissipation structure is provided with an installation hole connected to the receiving cavity, and the ultrasonic treatment tip further includes a buffer film assembly provided at the installation hole.

In an embodiment, the receiving cavity is provided with a guide rail slidingly cooperated with the transducer module.

In an embodiment, the transducer module includes a transducer bracket slidingly cooperated with the guide rail and a transducer provided at the transducer bracket, the transducer bracket is further provided with a push-against groove for the first end to extend into, the push-against groove is provided with two opposite push-against surfaces in an extension direction of the guide rail, and the first end is configured to push against the push-against surface.

In an embodiment, the transmission mechanism includes a swing rod that is rotatably passed through the shell and a push rod that is passed through the swing rod, one end of the swing rod is configured to be drivingly connected to the driving member, and another end of the swing rod is configured for the push rod to rotatably pass through, the push rod is configured to push against the push-against surface, and the push rod is provided in parallel with the push-against surface.

In an embodiment, two guide rails are provided, the two guide rails are provided in parallel, and the transducer module is slidably provided between the two guide rails;

and/or, the guide rail is provided with a guide groove, the transducer module is provided with a sliding protrusion that slidingly cooperates with the guide groove, a groove bottom of the guide groove is provided with a rib for the sliding protrusion to abut against, and the rib extends along an extension direction of the guide groove;

and/or, the guide rail and the shell are screw-locked;

and/or, the guide rail is provided with a guide groove, the transducer module is provided with a sliding protrusion that slidingly cooperates with the guide groove, and the openings at both ends of the guide groove are provided to be gradually expanded in a direction away from each other.

In an embodiment, the shell is provided with a via hole for the transmission mechanism to pass through, and the transmission mechanism covers the through hole.

In an embodiment, a hole wall of the via hole is provided with a spherical arc surface, and the transmission mechanism is provided with a covering portion forming a spherical pair with the spherical arc surface.

In the third aspect, the present application further provides an ultrasonic therapeutic apparatus, including:

a treatment tip including a cover body and a shell, the cover body and the shell are configured to limit a receiving cavity for receiving an ultrasonic transmission medium, and the cover body is provided with a heat dissipation structure in contact with the ultrasonic transmission medium;

a transducer module provided at the receiving cavity;

a handle including an outer shell and an end cap, the outer shell and the end cap are configured to limit an installation cavity, and the end cap is installed at the cover body and is provided with a thermal conductive portion thermally connected to the heat dissipation structure; and a refrigeration unit provided at the installation cavity and thermally connected to the thermal conductive portion to cool heat generated when the transducer module is working, the heat is transferred to the thermal conductive portion via the ultrasonic transmission medium and the heat dissipation structure.

In an embodiment, the cover body is provided with an avoidance opening, the heat dissipation structure includes a heat dissipation main body and a first heat dissipation convex portion connected to one side of the heat dissipation main body, and the first heat dissipation convex portion is configured to pass through the avoidance opening and thermally connect to the thermal conductive portion.

In an embodiment, the heat dissipation structure further includes a second heat dissipation convex portion connected to another side of the heat dissipation main body, and the second heat dissipation convex portion is configured to perform heat transfer with the ultrasonic transmission medium;

and/or, the heat dissipation main body is provided with a wire via hole for a wire harness of the transducer module to pass through and a caulking groove connected to the wire via hole, and the caulking groove is provided away from the first heat dissipation convex portion, and the treatment tip further includes a insulating shell and a circuit adapter board that are fixedly connected, and the insulating shell is adapted to the caulking groove and provided with a through hole connected to the wire via hole; the circuit adapter board is fixedly connected to an edge of the caulking groove, and a first plugging element is provided between the wire harness of the transducer module and the through hole;

and/or, the heat dissipation main body is provided with a via hole for ultrasonic transmission medium, the via hole for ultrasonic transmission medium is provided along a circumferentia of the heat dissipation main body, and the treatment tip further includes a second plugging element provided at the via hole for ultrasonic transmission medium;

and/or, the heat dissipation main body is provided with a buffer film assembly, and the buffer film assembly is configured to balance a pressure change in the receiving cavity;

and/or, the thermal conductive portion is protruding from a side of the end cap facing the cover body and provided to extend toward the avoidance opening.

In an embodiment, the refrigeration unit includes a semiconductor refrigeration assembly, the semiconductor refrigeration assembly includes a semiconductor refrigeration piece, a refrigeration piece cold plate and a refrigeration piece hot plate, and the semiconductor refrigeration piece is provided with an external power supply conducting wire; one side of the refrigeration piece cold plate is attached to a cold end of the semiconductor refrigeration piece, and another side of the refrigeration piece cold plate is attached to the thermal conductive portion; and the refrigeration piece hot plate is attached to a hot end of the semiconductor refrigeration piece to cool the hot end:

and/or, the refrigeration unit includes a water cooling assembly, and the water cooling assembly includes a water tank, the water tank is thermally connected to the thermal conductive portion, and the water tank is provided with coolants for heat exchange;

and/or, the refrigeration unit includes an air-cooled assembly, and the air-cooled assembly includes a heat pipe, a fin and a fan, a heat-absorbing end of the heat pipe is thermally connected to the thermal conductive portion, a heat dissipation end of the heat pipe is provided with the fin, and the fan is configured to make outside air exchange heat with the heat dissipation end of the heat pipe and the fin.

In an embodiment, the ultrasonic therapeutic apparatus further includes a driving member and a transmission assembly, the driving member is provided at the installation cavity, the transmission assembly includes a transmission mechanism and a linkage mechanism, the transmission mechanism is transmission connected to the driving member, the linkage mechanism is rotatably passed through the cover body and provided with a first end and a second end, the first end is drivingly connected to the transmission mechanism, the second end is transmission connected to the transducer module to drive the transducer module to perform reciprocating motion.

In an embodiment, the driving member includes a drive shaft, the transmission mechanism includes a swing bracket and a swing member, one end of the swing bracket is fixedly connected to the drive shaft, and another end of the swing bracket is transmission connected to the swing member, and the first end is provided with a buffer drill way for the swing member to be inserted and slidably passed through.

In an embodiment, the transmission mechanism further includes a slidingly connected adapter and a guide frame, the adapter is slidably and rotatably connected to the swing bracket, the adapter is fixedly connected with the swinging member, and the guide frame is passed through the adapter to make the adapter slide along the set path.

In an embodiment, the end of the swing bracket away from the drive shaft is provided with a limiting slot extending along the direction of the swing bracket, and the adapter is provided with a limit shaft slidably and rotatably passed through the limit slot;

and/or, the adapter includes a base and a pressure plate, the base is provided with a guide groove on a side away from the swing member, the pressure plate is detachably connected to the base to cover the guide groove, the guide frame passes through the guide groove, the groove bottom wall of the guide groove is an arc-shaped structure protruding toward a direction of the pressure plate;

and/or, the guide frame is an arch bridge structure;

and/or, the driving member, the transmission mechanism, the end cap and the cavity wall of the installation cavity jointly limit the assembly space, and the refrigeration unit is provided at the assembly space and is located above the thermal conductive portion.

In an embodiment, a guide rail is provided in the receiving cavity, the transducer module includes a transducer bracket slidingly cooperated with the guide rail, the transducer bracket is provided with a push-against groove for the second end to extend into, the push-against groove is provided with two opposite push-against surfaces in the extension direction of the guide rail, and the second end is configured to push against the push-against surface.

In an embodiment, the linkage mechanism includes a swing rod rotatably passed through the center of the cover body and a push rod passed through the swing rod, one end of the swing rod is drivingly connected to the transmission mechanism, another end of the swing rod is for the push rod to be rotatably passed through, the push rod is configured to push against the push-against surface, and the push rod and the push-against surface are provided in parallel:

and/or, a spherical pair structure is provided between the linkage mechanism and the cover body;

and/or, the guide rail is provided with a guide chute, the transducer bracket is provided with a sliding protrusion slidingly cooperating with the guide chute, the groove bottom of the guide chute is provided with a rib for the sliding protrusion to abut against, and the rib extends along an extension direction of the guide chute;

and/or, the transducer module further includes a transducer main body provided at the transducer bracket, the transducer bracket is fixed on the heat dissipation structure, and the sound-emitting surface of the transducer main body is a spherical structure or a tile surface structure.

In the fourth aspect, the present application further provides an ultrasonic therapeutic apparatus, including:

a treatment tip;

a handle including an outer shell and an end cap, the outer shell and the end cap are connected to form an installation cavity, the treatment tip is installed at the end cap, and the end cap is provided with a thermal conductive portion; and a heat dissipation device including a first heat dissipation module and a second heat dissipation module, the first heat dissipation module is provided at the treatment tip and is thermally connected to the thermal conductive portion, the second heat dissipation module is provided at the installation cavity and is thermally connected to the thermal conductive portion, and heat generated by the treatment tip is transferred to the second heat dissipation module via the first heat dissipation module and the thermal conductive portion in sequence.

In an embodiment, the treatment tip includes a shell and a cover body, and the shell and the cover body are connected to form a sealed accommodation cavity; and the first heat dissipation module is fixedly provided at the cover body and is at least partially exposed at the cover body to abut against the thermal conductive portion.

In an embodiment, the cover body is provided with a through-hole, a bump is provided at one side of the first heat dissipation module facing the handle, and the bump is exposed at the through-hole.

In an embodiment, the thermal conductive portion is protruding from one side of the end cap facing the treatment tip.

In an embodiment, the second heat dissipation module includes a heat pipe, and one end of the heat pipe is fixedly connected to the thermal conductive portion.

In an embodiment, the second heat dissipation module further includes a radiation fin group, the radiation fin group includes a plurality of radiation fins, and each of the radiation fins is provided at intervals and is provided in series at one end of the heat pipe away from the thermal conductive portion.

In an embodiment, two radiation fin groups are provided, and the two radiation fin groups are provided in series at the heat pipe at intervals.

In an embodiment, the second heat dissipation module further includes a fan, and an air outlet of the fan is provided facing the heat pipe.

In an embodiment, the outer shell includes a first shell portion and a second shell portion detachably connected to the first shell portion, the heat pipe is fixedly provided at the first shell portion, and the fan is provided at the second shell portion.

In an embodiment, the outer shell is provided with a heat dissipation hole, so that hot air inside the outer shell is discharged from the outer shell via the heat dissipation hole.

In an embodiment, a transducer module is provided inside the treatment tip, the transducer module is provided with a sound-emitting surface, the sound-emitting surface is a spherical structure;

and/or, the sound-emitting surface is a tile surface structure.

The present application further proposes an ultrasonic therapeutic apparatus, the ultrasonic therapeutic apparatus includes:

an ultrasonic treatment handle; and the aforementioned ultrasonic treatment tip, and the cover body of the ultrasonic treatment tip is connected to the ultrasonic treatment handle.

In the technical solution of the present application, the installation cavity limited by the outer shell and the cover body protects the inner shell. In addition, the outer shell and the cover body are also helpful in preventing the inner shell with relatively high temperature from coming into contact with the human body, the transducer is in the receiving cavity of the inner shell, the heat generated by the transducer will increase the temperature of the inner shell, however, due to the installation of the heat dissipation structure, part of the heat generated by the transducer will be transferred to the heat dissipation main body, the heat dissipation main body is connected to the first heat dissipation convex portion, and the heat dissipation main body can transfer heat to the first heat dissipation convex portion, the first heat dissipation convex portion is passed through the avoidance hole of the cover body. In this way, the heat inside the receiving cavity is relatively quickly discharged out of the ultrasonic treatment tip via the avoidance hole, thus, it can avoid that the temperature of the receiving cavity is relatively high, that is, the temperature inside the ultrasonic treatment tip is lowered, so that the pressure inside the ultrasonic treatment tip is relatively low, thereby reducing the possibility of the sound-permeable membrane bursting and prolonging the service life of the ultrasonic treatment tip. In addition, the cover body is configured to connect with the ultrasonic treatment handle, if a heat dissipation system is provided inside the ultrasonic treatment handle, the heat exported by the first heat dissipation convex portion can further be exported by utilizing the heat dissipation system inside the ultrasonic treatment handle.

BRIEF DESCRIPTION OF THE DRAWINGS

In order to explain the embodiments of the present application or the technical solutions in the existing technology more clearly, the accompanying drawings needed to be used in the description of the embodiments or the existing technology will be briefly introduced below. Obviously, the accompanying drawings in the following description are only some embodiments of the present application, other accompanying drawings can be obtained based on the provided accompanying drawings without exerting creative efforts for those of ordinary skill in the art.

Figure 1:
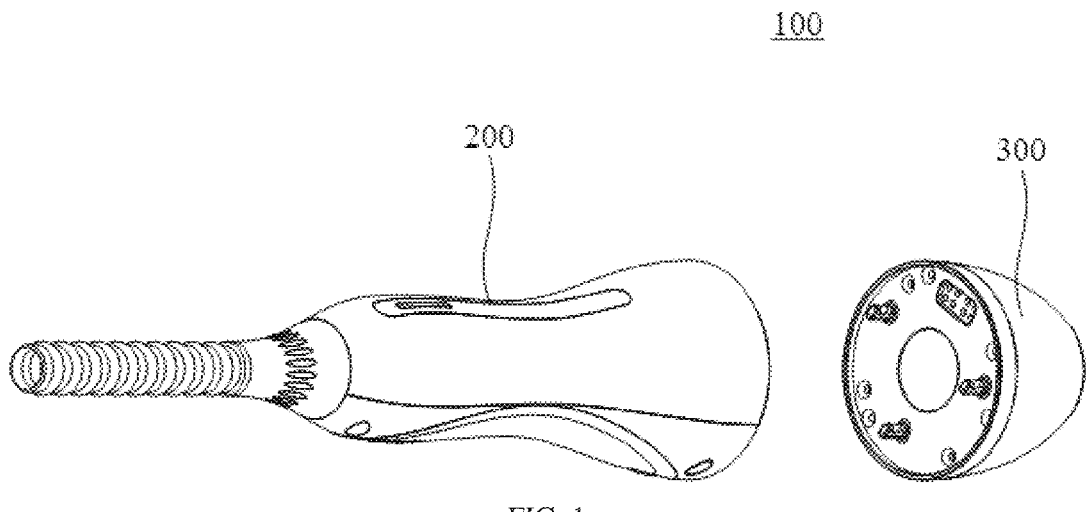
FIG. 1 is a structural schematic view of an ultrasonic therapeutic apparatus according to an embodiment of the present application.
Figure 2:
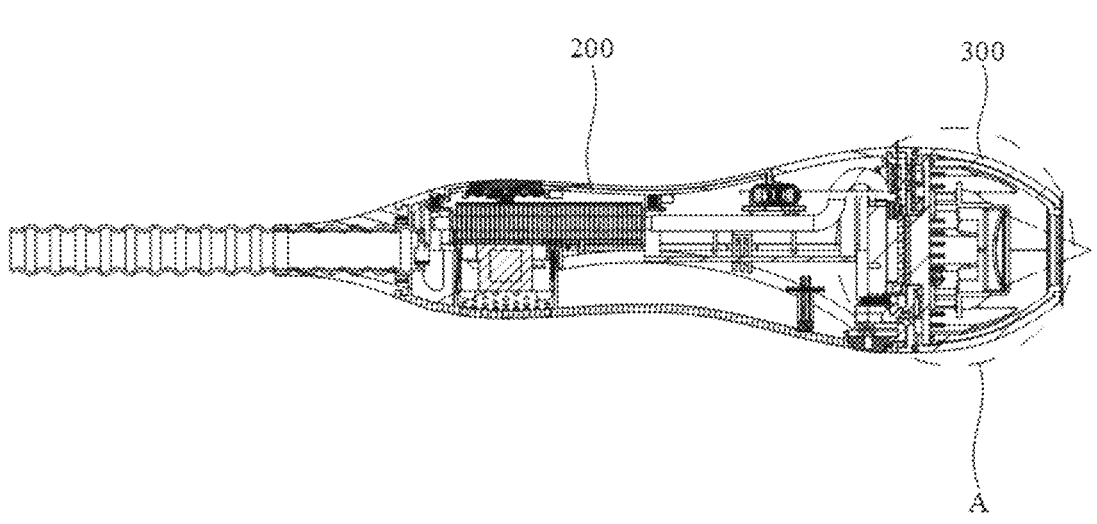
FIG. 2 is a section view of the ultrasonic therapeutic apparatus in FIG. 1 after assembling.
Figure 3:
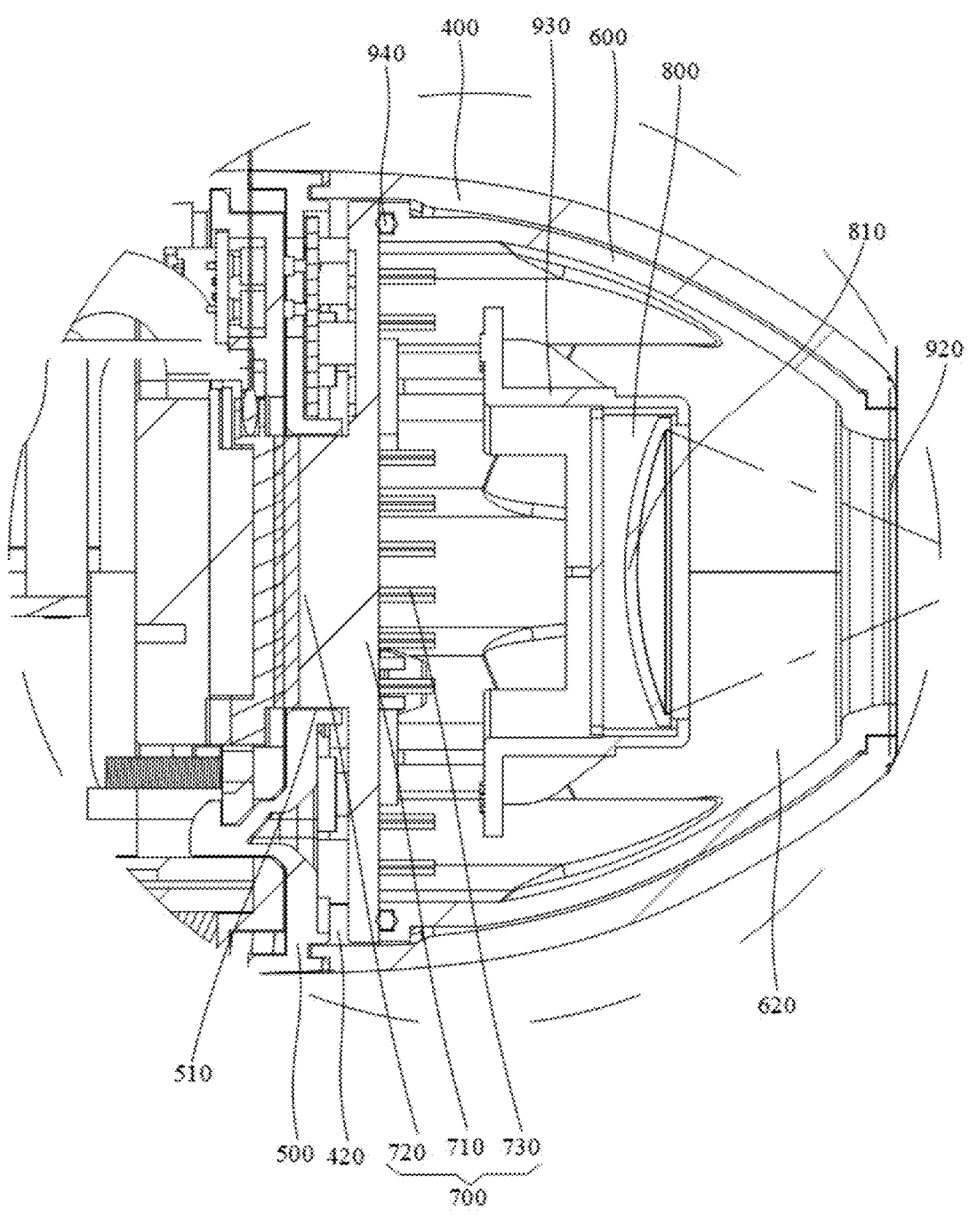
FIG. 3 is a partial enlarged view of the A in the FIG. 2.
Figures 4, 5:
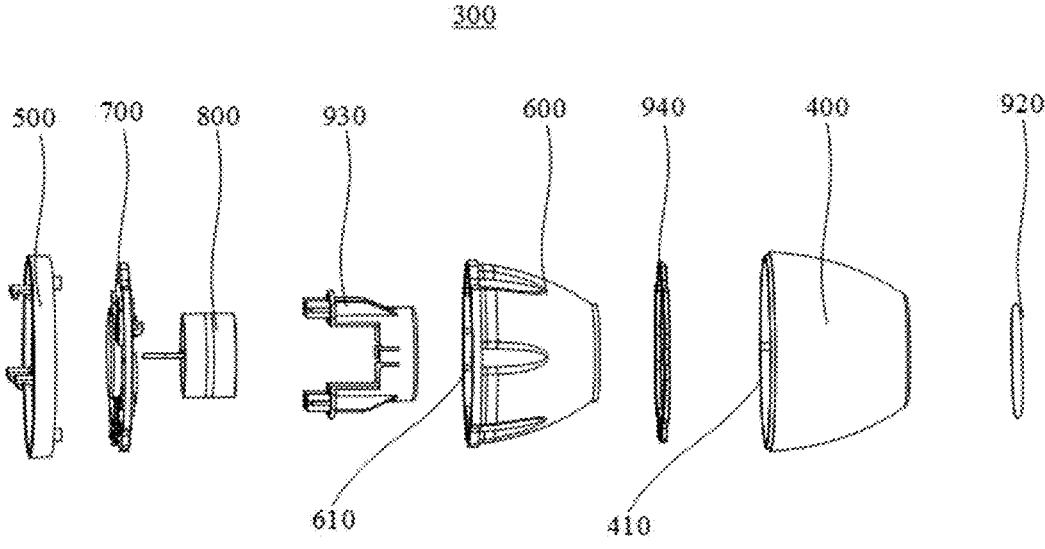
FIG. 4 is an exploded view of an ultrasonic treatment tip in FIG. 1.
FIG. 5 is a structural schematic view of a heat dissipation structure from a perspective in FIG. 4.
Figure 6:
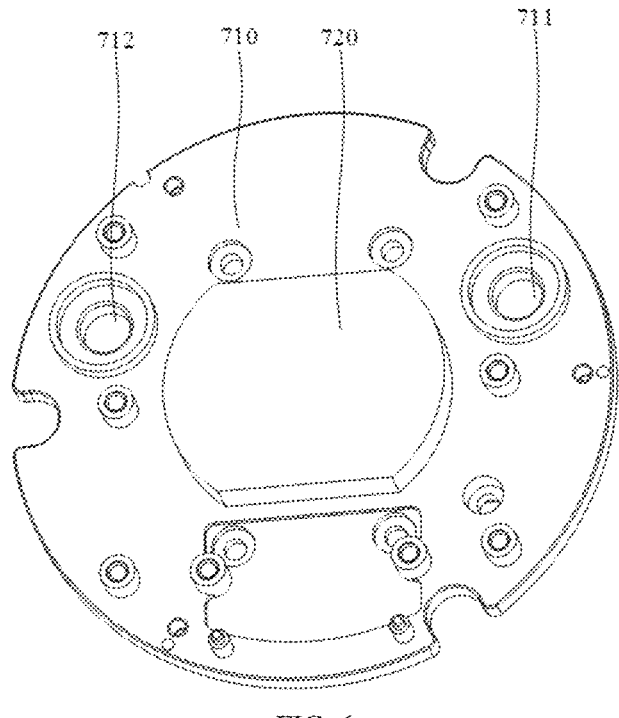
FIG. 6 is a structural schematic view of a heat dissipation mechanism from another perspective in FIG. 4.
Figure 7:
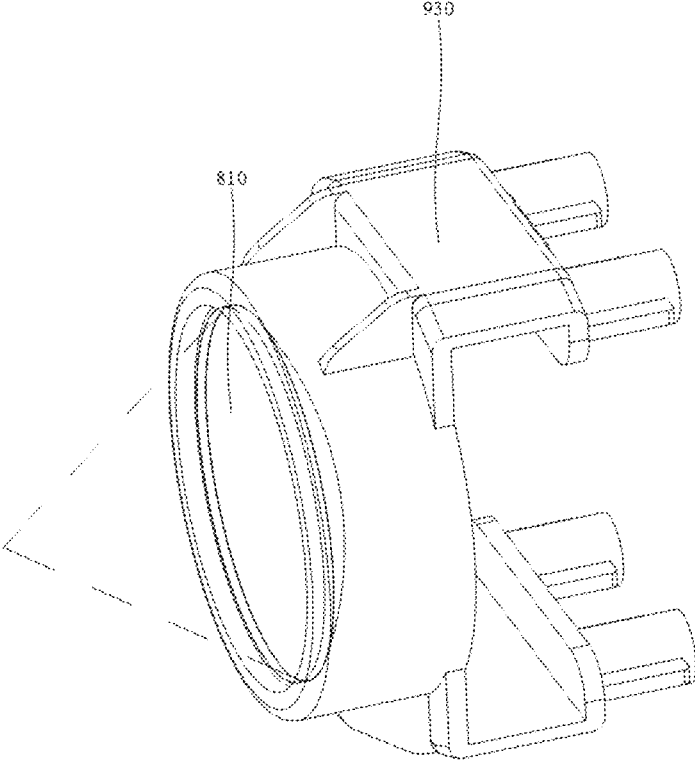
FIG. 7 is a structural schematic view of a transducer and a transducer bracket after assembling according to an embodiment.
Figure 8:
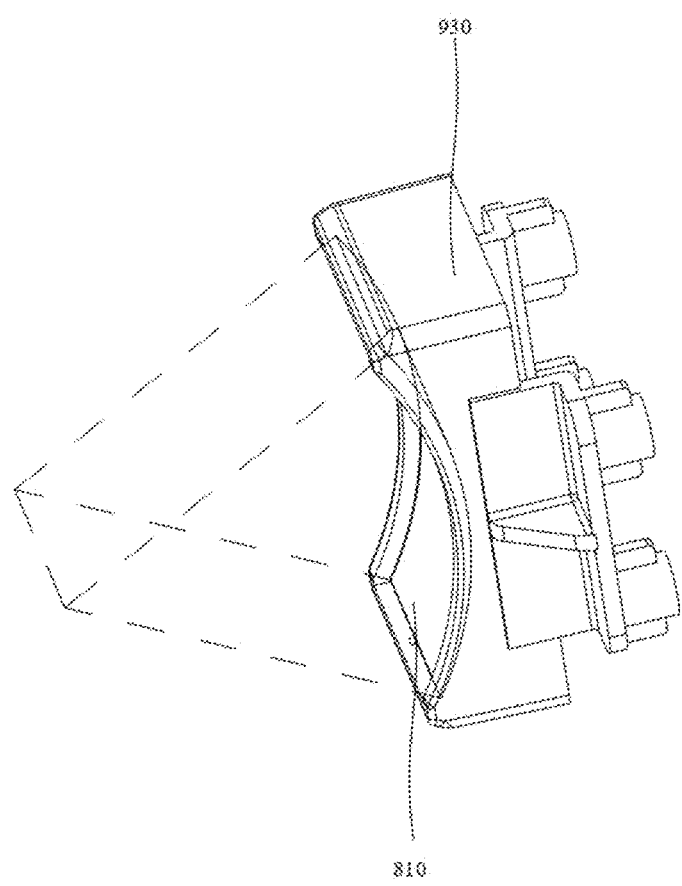
FIG. 8 is a structural schematic view of the transducer and the transducer bracket after assembling according to another embodiment.
Figure 9:
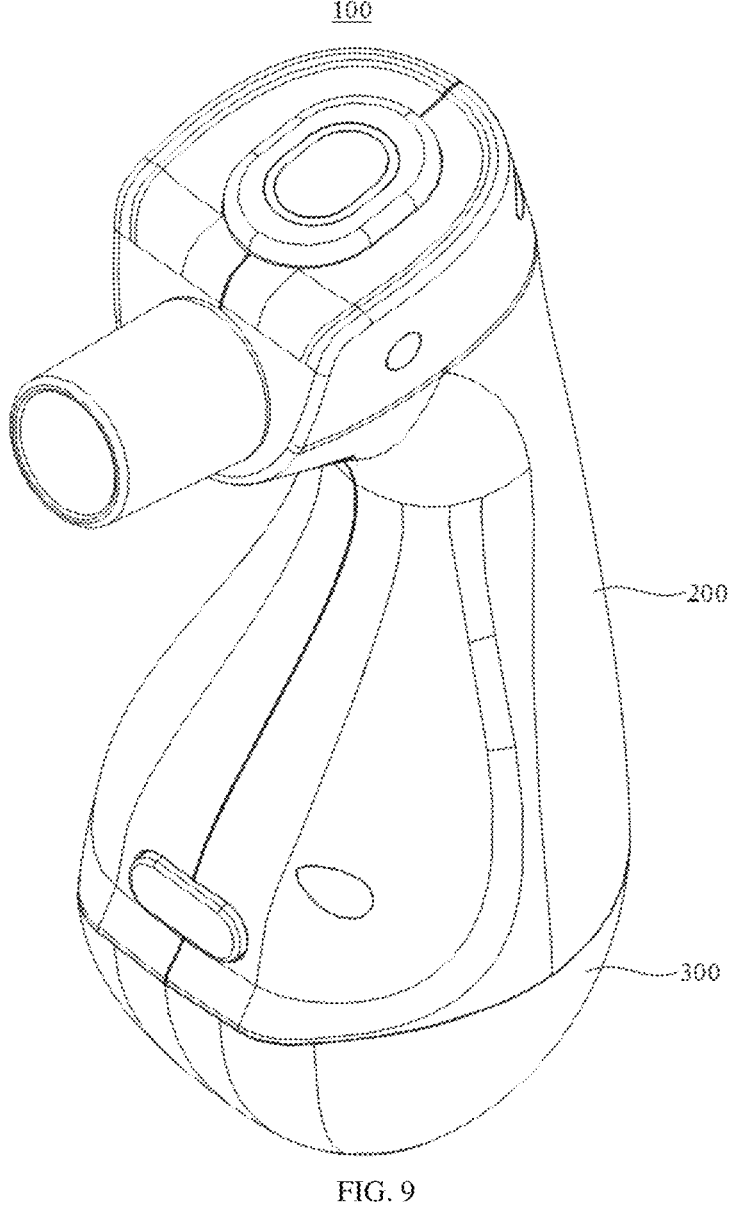
FIG. 9 is a structural schematic view of the ultrasonic therapeutic apparatus according to another embodiment of the present application.
Figure 10:
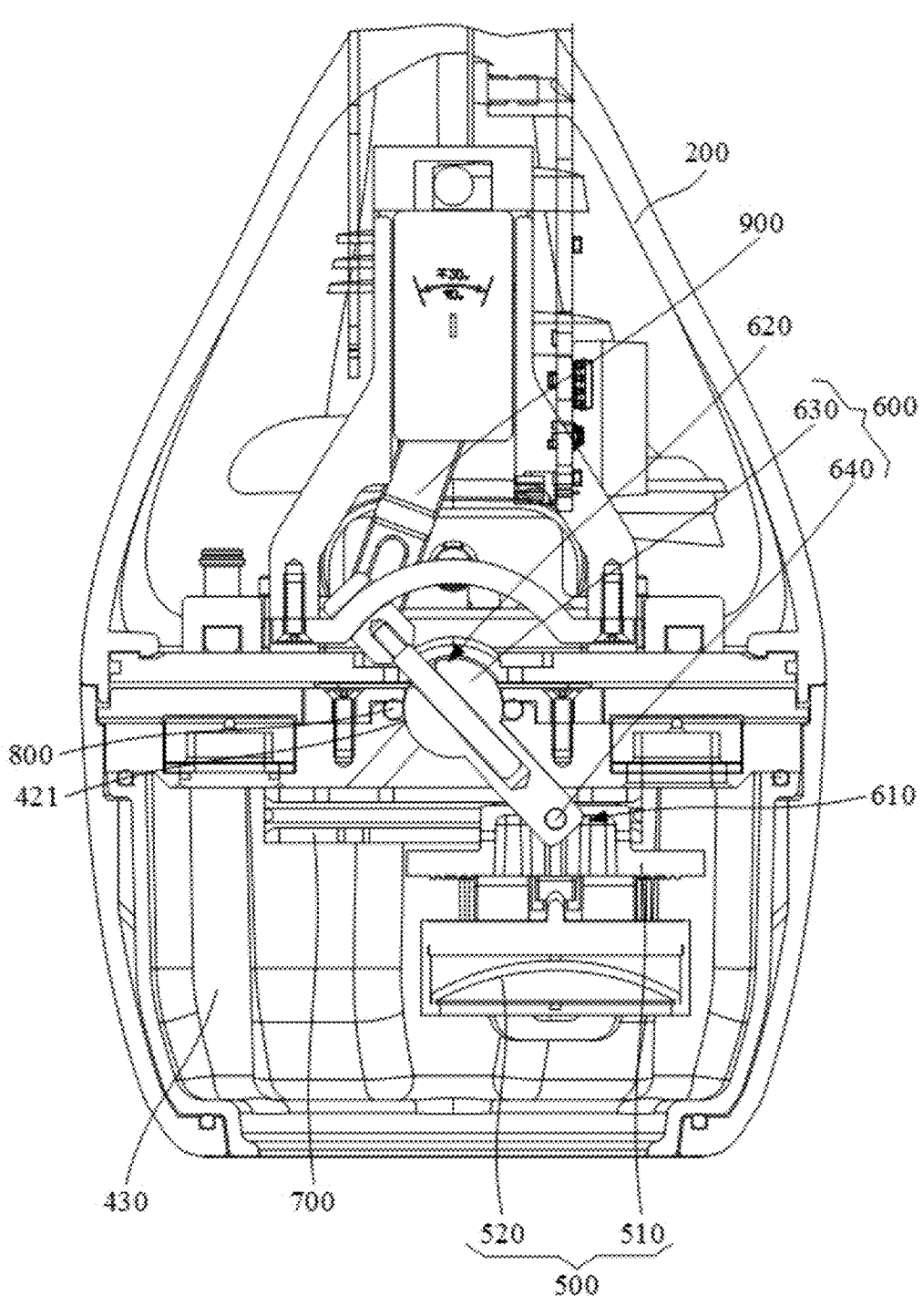
FIG. 10 is a section view of partial structure of the ultrasonic therapeutic apparatus in FIG. 9.
Figure 11:
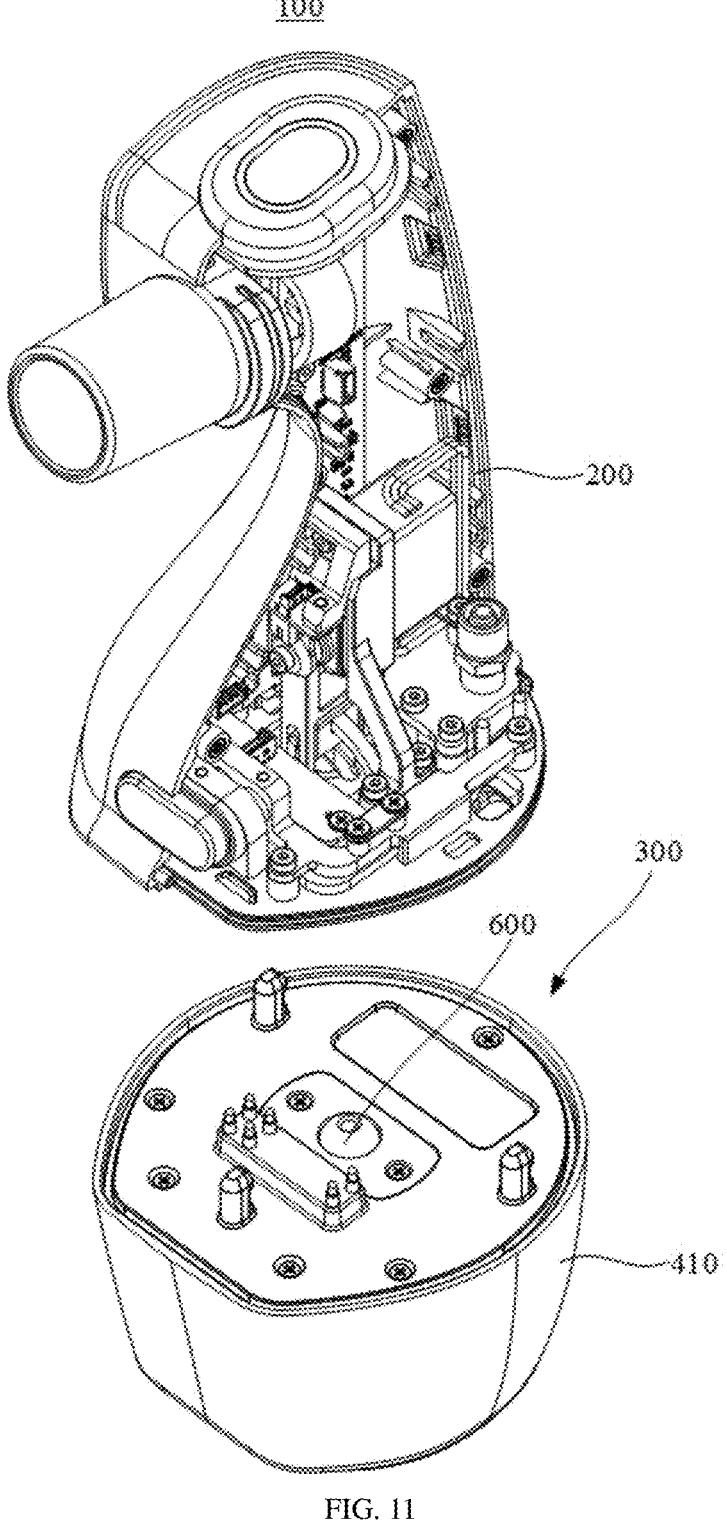
FIG. 11 is an exploded view of the ultrasonic therapeutic apparatus in FIG. 9.
Figure 12:
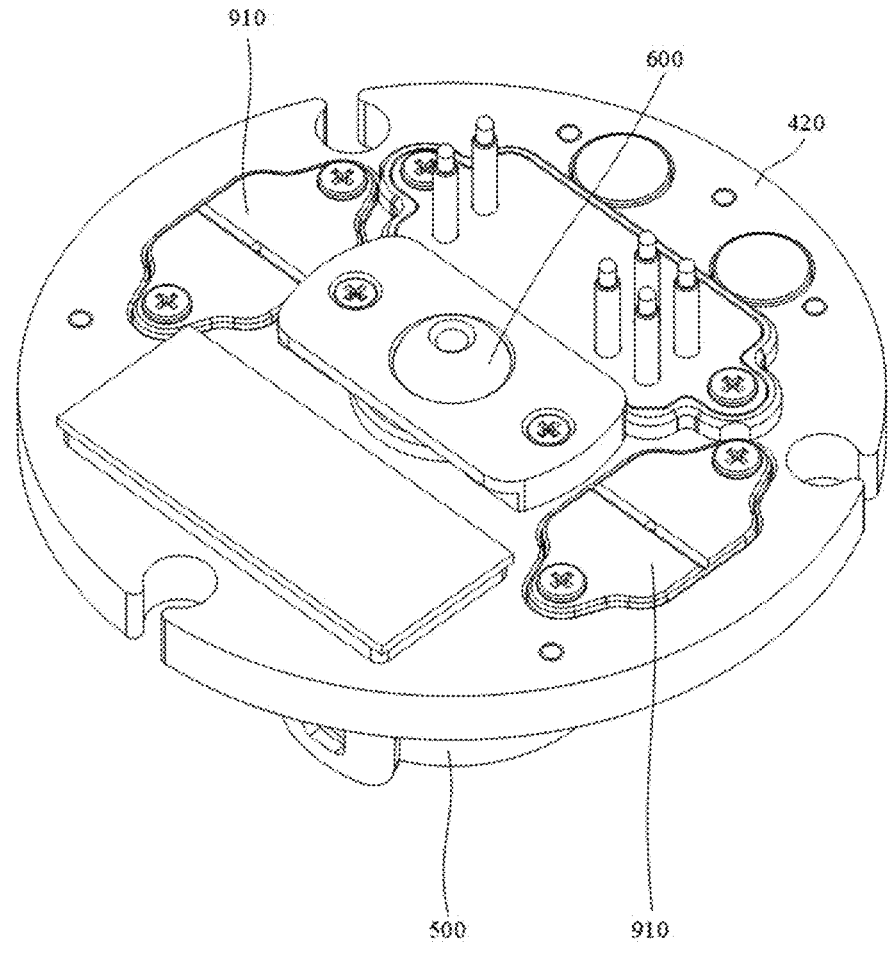
FIG. 12 is a structural schematic view of the ultrasonic treatment tip after hiding a shell from a perspective in FIG. 11.
Figure 13:
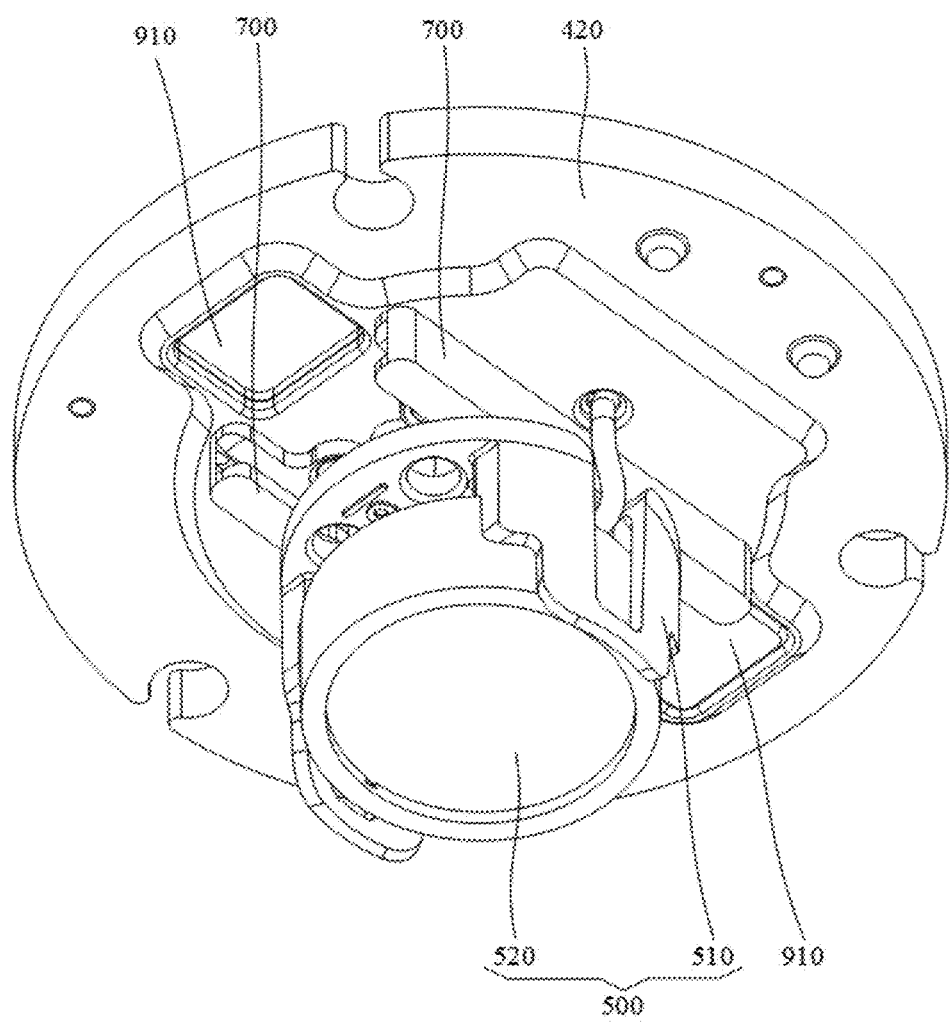
FIG. 13 is a structural schematic view of the ultrasonic treatment tip after hiding a shell from another perspective in FIG. 11.
Figure 14:
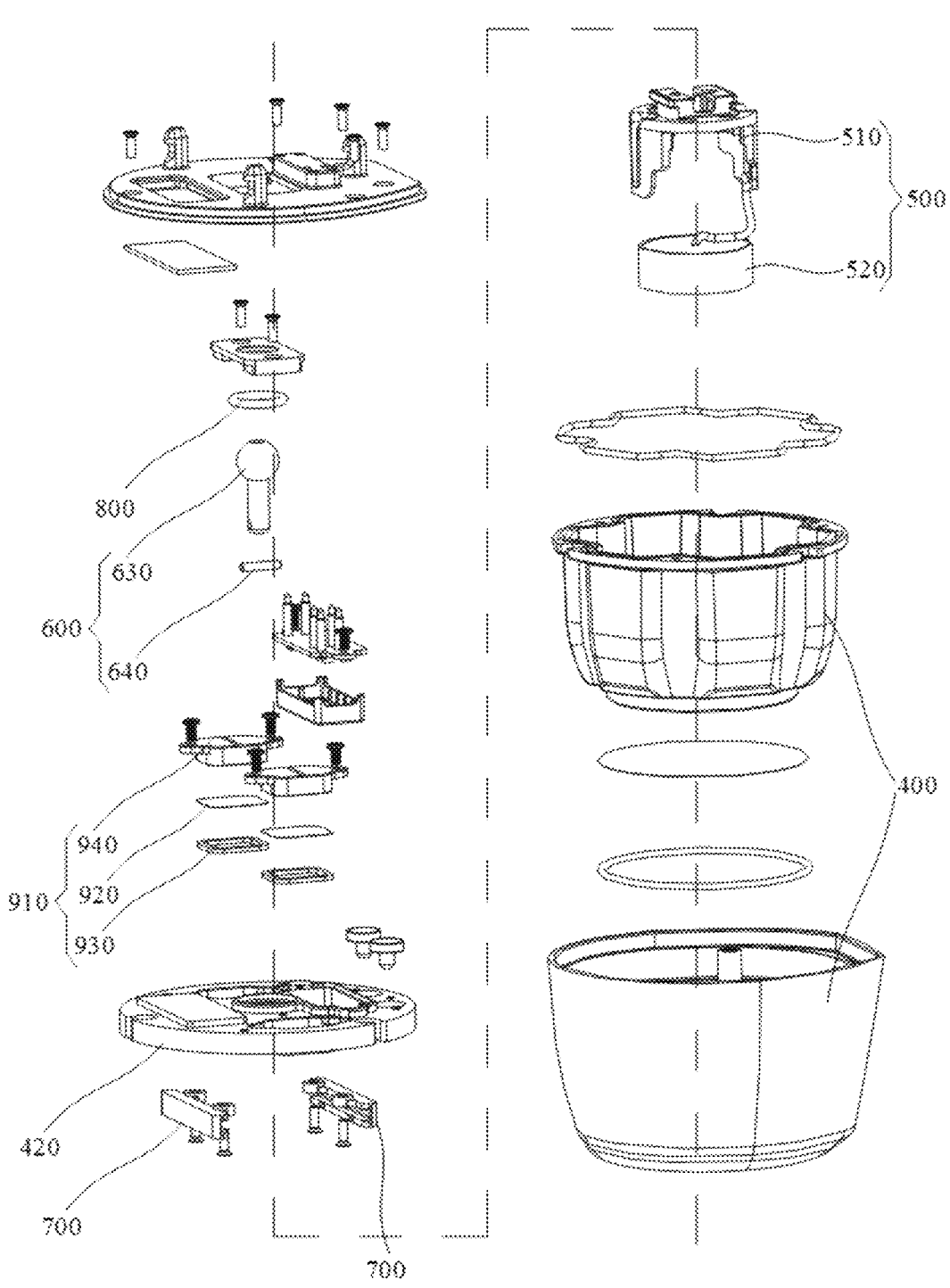
FIG. 14 is an exploded view of the ultrasonic treatment tip in FIG. 11.

The realization of the purpose, functional features and advantages of the present application will be further described in conjunction with the embodiments and with reference to the accompanying drawings.

DETAILED DESCRIPTION OF THE EMBODIMENTS

The technical solutions in the embodiments according to the present application will be clearly and completely described below in conjunction with the accompanying drawings in the embodiments according to the present application, and it is clear that the described embodiments are only a part of the embodiments according to the present application, and not all of the embodiments. Based on the embodiments in the present application, all other embodiments obtained by those of ordinary skill in the art without making creative labor fall within the scope of the present application.

It should be noted that in the embodiment of the present application, all directional indications (such as up, down, left, right, front, back or the like) are only used to explain the relative positional relationship, movement and so on between various components in a specific posture (as shown in the accompanying drawings). If the specific posture changes, the directional indication will also change accordingly.

In the present application, unless otherwise clearly stated and limited, the terms "connection", "fixed" and so on should be understood in a broad sense. For example, "connection" can be a fixed connection, a detachable connection or an integral body; it can be a mechanical connection or an electrical connection; it can be a direct connection or an indirect connection through an intermediate medium; it can be contact, or an internal connection between two components, or the interaction between two components, unless otherwise clearly limited. For those of ordinary skill in the art, the specific meanings of the above terms in the present application can be understood according to the specific circumstances.

In addition, in the embodiment of the present application, if there are descriptions involving "first", "second" or the like, the descriptions of "first", "second" or the like are only for descriptive purposes and cannot be understood as indicating or implying the relative importance or implicitly indicating the quantity of the technical features indicated. Therefore, features defined as "first" and "second" may explicitly or implicitly include at least one of these features. In addition, the meaning of "and/or" appearing in the entire text includes three parallel solutions, taking "A and/or B" as an example, it includes solution A, or solution B, or a solution that satisfies both A and B at the same time. In addition, the technical solutions of various embodiments can be combined with each other, but it is based on that those of ordinary skill in the art can realize. When the combination of technical solutions is contradictory or cannot be realized, it should be considered that such combination of technical solutions does not exist and is not within the protection scope claimed by the present application.

The ultrasonic therapeutic apparatus includes an ultrasonic treatment tip, the ultrasonic treatment tip is equipped with a transducer. By converting the electrical energy into the sound energy, the transducer can emit ultrasonic waves towards the sound-permeable membrane to transmit the ultrasonic waves to the human body. The transducer will generate heat when working, which causes the temperature inside the ultrasonic treatment tip to be relatively high, thereby resulting in a relatively high pressure inside the ultrasonic treatment tip, which can easily cause the sound-permeable membrane to burst. To this end, the present application proposes an ultrasonic treatment tip, aiming to reduce the temperature inside the ultrasonic treatment tip, thus making the pressure inside the ultrasonic treatment tip relatively low and reducing the possibility of the sound-permeable membrane bursting.

Ultrasonic therapeutic apparatus is a physical therapy instrument commonly configured for skin treatment and conditioning, the ultrasonic therapeutic apparatus includes an ultrasonic treatment tip and an ultrasonic treatment handle that is connected to the ultrasonic treatment tip. Ultrasonic waves are emitted from the transducer module inside the ultrasonic treatment tip, in order to make the area to be treated undergo physiotherapy, the operator needs to frequently move the ultrasonic therapeutic apparatus to drive the ultrasonic treatment tip to move, so as to make the ultrasonic waves pass through all areas to be treated. However, moving the ultrasonic therapeutic apparatus frequently will greatly increase the operator's workload. To this end, the present application proposes an ultrasonic treatment tip, aiming to reduce the number of times the ultrasonic therapeutic apparatus needs to be moved, thereby reducing the workload of the operator.

Referring to FIG. 1 to FIG. 6, in an embodiment according to the present application, the ultrasonic treatment tip 300 includes:

an outer shell 401 provided with a first port 410A;

a cover body 501 covering the first port 410A, the cover body 501 and the outer shell 401 are configured to limit an installation cavity 421, the cover body 501 is provided with an avoidance hole 510A connected to the installation cavity 421, and the cover body 501 is connected to the ultrasonic treatment handle 200;

an inner shell 600A provided at the installation cavity 421, the inner shell 600A is provided with a receiving cavity 430 for receiving an ultrasonic transmission medium, and the receiving cavity 430 is provided with a second port 610A;

a heat dissipation structure 420 including a heat dissipation main body 710A provided at the second port 610A and a first heat dissipation convex portion 720 passed through the avoidance hole 510A, the first heat dissipation convex portion 720 is connected to the heat dissipation main body 710A;

a sound-permeable membrane 920A, the ultrasonic treatment tip 300 is provided with a sound-permeable opening passed through the outer shell 401 and the inner shell 600A, and the sound-permeable membrane 920A is provided at the sound-permeable opening; and a transducer 800A received at the receiving cavity 430, the transducer 800A is provided with a vibrating sound-emitting surface 810 provided toward the sound-permeable membrane 920A.

In the technical solution of the present application, the installation cavity 421 limited by the outer shell 401 and the cover body 501 protects the inner shell 600A. In addition, the outer shell 401 and the cover body 501 are also helpful in preventing the inner shell 600A with a relatively high temperature from coming into contact with the human body. The transducer 800A is in the receiving cavity 430 of the inner shell 600A, the heat generated by the transducer 800A will increase the temperature of the inner shell 600A. However, due to the installation of the heat dissipation structure 420, part of the heat generated by the transducer 800A will be transferred to the heat dissipation main body 710A, the heat dissipation main body 710A is connected to the first heat dissipation convex portion 720, the heat dissipation main body 710A can transfer heat to the first heat dissipation convex portion 720, the first heat dissipation convex portion 720 is passed through the avoidance hole 510A of the cover body 501, in this way, the heat inside the receiving cavity 430 is relatively quickly discharged out of the ultrasonic treatment tip 300 via the avoidance hole 510A, thus, it can avoid that the temperature of the receiving cavity 430 is relatively high, that is, the temperature inside the ultrasonic treatment tip 300 decreases, thereby making the pressure inside the ultrasonic treatment tip 300 relatively low, reducing the possibility of the sound-permeable membrane 920A bursting and prolonging the service life of the ultrasonic treatment tip 300. In addition, the cover body 501 is configured to connect with the ultrasonic treatment handle 200, if a heat dissipation system is provided inside the ultrasonic treatment handle 200, the heat exported by the first heat dissipation convex portion 720 can further be exported by utilizing the heat dissipation system in the ultrasonic treatment handle 200.

It is worth mentioning that the ultrasonic transmission medium can be, but is not limited to, water, and the transducer 800A can transfer heat to the heat dissipation structure 420 through water.

In order to speed up the transfer of the heat generated by the transducer 800A to the outside of the ultrasonic treatment tip 300, in an embodiment, the heat dissipation structure 420 further includes a second heat dissipation convex portion 730 provided at the receiving cavity 430, thus, increasing the contact area between the heat dissipation structure 420 and the ultrasonic transmission medium by the second heat dissipation convex portion 730, so that a large amount of heat is exported from the heat dissipation structure 420 to the outside of the ultrasonic treatment tip 300. However, the present design is not limited to this, in other embodiments, the area where the heat dissipation main body 710A is exposed at the receiving cavity 430 may be provided with a frosted layer, thereby increasing the contact area between the heat dissipation main body 710A and the ultrasonic transmission medium.

In an embodiment, the ultrasonic treatment tip 300 further includes the ultrasonic transmission medium received at the receiving cavity 430, and the second heat dissipation convex portion 730 is configured to be immersed into the ultrasonic transmission medium. In this way, the second heat dissipation convex portion 730 can fully exchange heat with the ultrasonic transmission medium and quickly dissipate the heat of the ultrasonic transmission medium, which is conducive to improving the heat dissipation efficiency of the ultrasonic treatment tip 300. Specifically, the ultrasonic transmission medium can be filled in the receiving cavity 430, so that the second heat dissipation convex portion 730 can always be in contact with the ultrasonic transmission medium to cause the heat exchange therebetween consistantly, which is conducive to reducing the temperature of the ultrasonic treatment tip 300.

In an embodiment, a plurality of the second heat dissipation convex portions 730 are provided. It can be understood that, the greater the number of the second heat dissipation convex portion 730, the greater the contact area between the heat dissipation structure 420 and the ultrasonic transmission medium, so that the more heat is exported from the heat dissipation structure 420 to the outside of the ultrasonic treatment tip 300, thus the more obvious the heat dissipation effect will be.

In an embodiment, the heat dissipation main body 710A is configured to cover the second port 610A, the heat dissipation main body 710A is provided with a wire via hole 711A for a wire harness of the transducer 800A to pass through, and the ultrasonic treatment tip 300 further includes a first plugging element provided between the wire via hole 711A and the wire harness of the transducer 800A. In this way, the heat dissipation structure 420 not only undertakes the heat dissipation function, but also undertakes the wire passing function, which enriches the functions of the heat dissipation structure 420, and can avoid opening the wire via hole 711A on the inner shell 600A, which is beneficial for the inner shell 600A to maintain structural integrity, so that the inner shell 600A has relatively high structural strength. It can be understood that after the wire harness passes through the wire via hole 711A, there is a gap between the wire harness and the wire via hole 711A, in order to avoid leakage of the ultrasonic transmission medium, the ultrasonic treatment tip 300 is further provided with a first plugging element to make the tightness of the receiving cavity 430 relatively high. Certainly, in other embodiments, if necessary, the wire via hole 711A can be passed through the outer shell 401 and the inner shell 600A; or, the heat dissipation main body 710A is provided with an avoidance area, the cover body 501 is provided with a wire via hole 711A for a wire harness of the transducer 800A to pass through, the ultrasonic treatment tip 300 further includes a first plugging element provided between the wire via hole 711A and the wire harness of the transducer 800A, and the wire via hole 711A is exposed at the avoidance area. It should be pointed out that the avoidance area can be in the shape of a hole, the avoidance area is provided at the middle of the heat dissipation main body 710A; the avoidance area can also be in the shape of a notch, and the avoidance area is provided at the circumference of the heat dissipation main body 710A.

In an embodiment, the heat dissipation main body 710A is provided with an ultrasonic transmission medium via a hole 712A, and the ultrasonic treatment tip 300 further includes a second plugging element provided at the ultrasonic transmission medium via the hole 712A. In this way, the heat dissipation structure 420 not only undertakes the heat dissipation function, but also undertakes the function of introducing the ultrasonic transmission medium into the receiving cavity 430, which enriches the functions of the heat dissipation structure 420, and can avoid opening the ultrasonic transmission medium via the hole 712A on the inner shell 600A, which is beneficial for the inner shell 600A to maintain structural integrity, so that the inner shell 600A has relatively high structural strength. After the ultrasonic transmission medium is introduced into the receiving cavity 430, the ultrasonic transmission medium via the hole 712A is blocked by the second plugging element, thereby preventing leakage of the ultrasonic transmission medium. Certainly, in other embodiments, if necessary, the ultrasonic transmission medium hole can be passed through the outer shell 401 and the inner shell 600A; or, the heat dissipation main body 710A is provided with an avoidance area, the cover body 501 is provided with an ultrasonic transmission medium via the hole 712A, the ultrasonic treatment tip 300 further includes a second plugging element provided at the ultrasonic transmission medium via the hole 712A, and the ultrasonic transmission medium via the hole 712A is exposed at the avoidance area. It should be pointed out that the avoidance area can be in the shape of a hole, the avoidance area is provided at the middle of the heat dissipation main body 710A; the avoidance area can also be in the shape of a notch, and the avoidance area is provided at the circumference of the heat dissipation main body 710A.

In an embodiment, the transducer 800A is provided with a vibrating sound-emitting surface 810 that emits ultrasonic waves, and the vibrating sound-emitting surface 810 is provided to be recessed, the recessed setting of the vibrating sound-emitting surface 810 is conducive to converging the ultrasonic waves emitted by the transducer 800A, so that the energy of the ultrasonic waves reaching the human body is relatively concentrated, which is conducive to improving the therapeutic effect. Certainly, in other embodiments, a sound collecting device can be provided, so that the energy of the ultrasonic waves reaching the human body is relatively concentrated after the ultrasonic waves emitted by the transducer 800A pass through the sound collection device.

Figure 15:
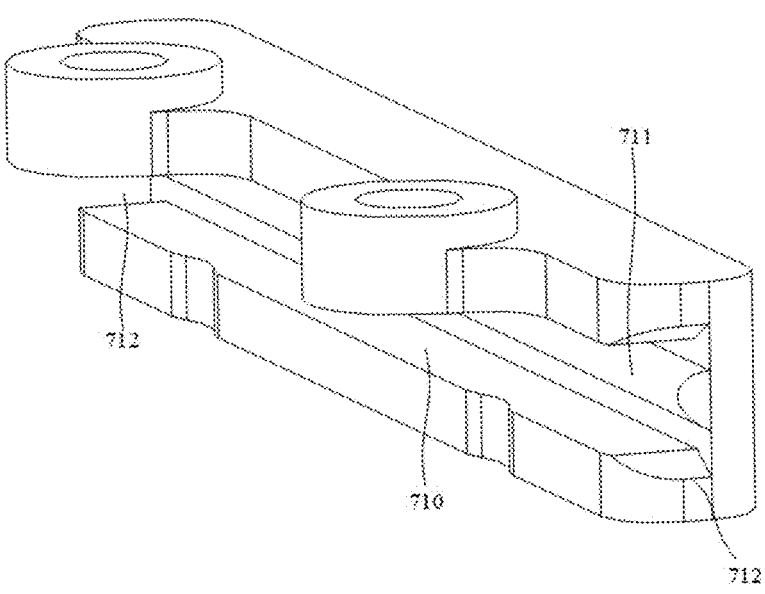
FIG. 15 is a structural schematic view of a guide rail in FIG. 11.
Figure 16:
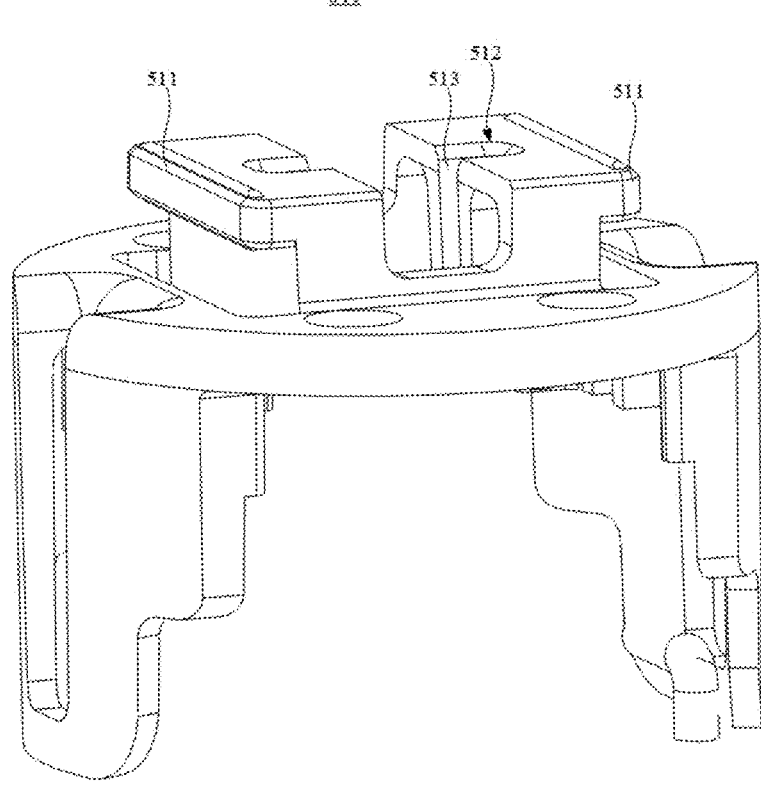
FIG. 16 is a structural schematic view of the transducer bracket in FIG. 11.

Referring to FIG. 15 and FIG. 16 together, in an embodiment, the vibrating sound-emitting surface 810 is provided to be a spherical arc surface or a tile surface. When the vibrating sound-emitting surface 810 is provided to be a spherical arc surface, the ultrasonic waves will converge at one point, which is conducive to doing the treatment with relatively concentrated ultrasonic energy to the user's area to be treated. When the vibrating sound-emitting surface 810 is provided to be a tile surface, the ultrasonic waves will converge on a line, in this way, when moving the ultrasonic treatment tip 300, the area swept by the line is a surface, which is conductive to increasing the speed of treating users.

In an embodiment, the sound-permeable membrane 920A is sandwiched between the outer shell 401 and the inner shell 600A. In this way, the sound-permeable membrane 920A can be effectively prevented from falling off. Certainly, in other embodiments, the sound-permeable membrane 920A is adhered to the circumferentia of the sound-permeable opening.

In an embodiment, the ultrasonic treatment tip 300 further includes a transducer bracket 930A provided at the heat dissipation main body 710A, and the transducer 800A is provided at the transducer bracket 930A. The transducer bracket 930A can prevent the transducer 800A from shaking easily during use of the ultrasonic treatment tip 300, it can achieve relatively precise control of the ultrasonic waves reaching the treatment area, which is beneficial to improving the treatment effect. In addition, the transducer bracket 930A is provided at the heat dissipation main body 710A, which is convenient for assembling the ultrasonic treatment tip 300. Specifically, after the transducer 800A is installed at the transducer bracket 930A, and the transducer bracket 930A is installed at the heat dissipation main body 710A, during the heat dissipation main body 710A is covered with the second port 610A, both the transducer 800A and the transducer bracket 930A then enter the receiving cavity 430, which is very convenient, and the transducer 800A and the transducer bracket 930A do not need to be installed in the inner shell 600A. It is understandable that the inner shell 600A has a small space and is inconvenient to operate. Certainly, if necessary, the transducer bracket 930A can also be provided at the inner wall surface of the inner shell 600A.

Although the heat dissipation main body 710A is covered with the second port 610A, there may still be a gap between the heat dissipation main body 710A and the inner shell 600A. For this reason, in an embodiment, a second sealing ring 940A is provided between the inner shell 600A and the heat dissipation main body 710A. In this way, the tightness of the receiving cavity 430 can be improved and leakage of the ultrasonic transmission medium can be avoided. Specifically, in an embodiment, the inner shell 600A is provided with an accepting groove at the circumferentia of the second port 610A to receive the second sealing ring 940A, the direction of the groove opening of the accepting groove is parallel to the direction of the second port 610A, and the second sealing ring 940A abuts against the heat dissipation main body 710A. In this way, when the heat dissipation main body 710A is covered with the second port 610A, the heat dissipation main body 710A also abuts against the second sealing ring 940A, which is very convenient to install the ultrasonic treatment tip 300.

Referring to FIG. 9 to FIG. 14, in an embodiment according to the present application, the ultrasonic treatment tip 300 includes:

a shell 400 provided with a receiving cavity 430, and the shell 400 is provided with a heat dissipation structure 420;

a transducer module 500 provided at the receiving cavity 430; and a transmission mechanism 600 rotatably passing through the shell 400, the transmission mechanism 600 is provided with a first end 610 and a second end 620, the first end 610 is transmission connected to the transducer module 500, the second end 620 is configured to drivingly connected to a driving member 900, and the transmission mechanism 600 is configured to drive the transducer module 500 to perform reciprocating motion.

In the technical solution of the present application, the transmission structure can realize swing under the power provided by the driving member 900, thereby driving the transducer module 500 that is transmission connected to the first end 610 of the transmission structure to perform reciprocating motion, the transducer module 500 is configured to emit ultrasonic waves, when the transducer module 500 is reciprocating, the area covered by the ultrasonic waves emitted by the transducer 520 is relatively wide, for the area to be treated of the same size during physical therapy, the number of times the operator moves the ultrasonic therapeutic apparatus 100 can be reduced, thereby reducing the operator's workload. In addition, the heat generated when the transducer module 500 is working makes the temperature inside the receiving cavity 430 relatively high, by providing the heat dissipation structure 420, it is conducive to dissipating the heat from the receiving cavity 430, so that the temperature inside the receiving cavity 430 is relatively low, so that the pressure inside the receiving cavity 430 is relatively low, thereby reducing the possibility of sound-permeable membrane bursting and prolonging the service life of ultrasonic treatment tip 300. It can be understood that the ultrasonic treatment tip 300 is usually provided with a sound-permeable membrane exposed at the receiving cavity 430, the transducer module 500 is provided with a vibrating sound-emitting surface set toward the sound-permeable membrane to emit ultrasonic waves, and the ultrasound waves can propagate through the sound-permeable membrane to the area to be treated.

Referring to FIG. 15 together, in an embodiment, the receiving cavity 430 is provided with a guide rail 700 slidingly cooperated with the transducer module 500. In this way, under the guidance function of the guide rail 700, the transducer module 500 can slide comparatively smoothly, which is beneficial for the area to be treated to obtain more precise treatment.

Referring to FIG. 16 together, in an embodiment, the transducer module 500 includes a transducer bracket 510 slidably cooperated with the guide rail 700 and a transducer 520 provided at the transducer bracket 510, the transducer bracket 510 is further provided with a push-against groove 512 for the first end 610 to extend into, the push-against groove 512 is provided with two opposite push-against surfaces 513 in an extension direction of the guide rail 700, and the first end 610 is configured to push against the push-against surface 513. In this way, the transmission mechanism 600 can push against different push-against surfaces 513 via the first end 610, so that the transducer 520 can perform reciprocating motion along the guide rail 700.

In an embodiment, the first end 610 can slide on the push-against surface 513, when the trajectory of the guide rail 700 is inconsistent with the trajectory of the first end 610, the swing of the transducer module 500 can be converted into a motion along the trajectory of the guide rail 700 by the sliding of the first end 610 on the push-against surface 513, which can effectively avoid interference between the transmission mechanism 600 and the transducer module 500, for example, the trajectory of the guide rail 700 may be, but is not limited to, a straight line. However, the design is not limited to this, in other embodiments, the first end 610 is fixed on the transducer module 500.

In an embodiment, the transmission mechanism 600 includes a swing rod 630 that is rotatably passed through the shell 400 and a push rod 640 that is passed through the swing rod 630, one end of the swing rod 630 is configured to be drivingly connected to the driving member 900, and another end of the swing rod 630 is configured for the push rod 640 to rotatably pass through, the push rod 640 is configured to push against the push-against surface 513, and the push rod 640 is provided in parallel with the push-against surface 513. The driving member 900 is drivingly connected to one end of the swing rod 630 to drive the swing rod 630 to swing, the push rod 640 is rotatably passed through another end of the swing rod 630, so that the swing rod 630 can drive the push rod 640 to swing. Since the push rod 640 and the push-against surface 513 are provided in parallel, when the push rod 640 pushes against the push-against surface 513, the push rod 640 can roll relatively with the push-against surface 513 to reduce the resistance between the push rod 640 and the push-against surface 513, so that the transmission mechanism 600 drives the transducer module 500 to reciprocate relatively smoothly. It can be understood that in this embodiment, the push rod 640 is equivalent to the first end 610 mentioned above. However, the present design is not limited to this, in other embodiments, the push rod 640 can be replaced by a sphere, and the sphere and the swing rod 630 form a spherical pair.

In an embodiment, two guide rails 700 are provided, the two guide rails 700 are provided in parallel, and the transducer module 500 is slidably provided between the two guide rails 700. In this way, the transducer module 500 can slide relatively smoothly, and at the same time, it also can avoid the force of the transducer module 500 acting on the guide rail 700 to be relatively concentrated.

In an embodiment, the guide rail 700 is provided with a guide groove 710, and the transducer module 500 is provided with a sliding protrusion 511 that slidingly cooperates with the guide groove 710, a groove bottom of the guide groove 710 is provided with a rib 711 for the sliding protrusion 511 to abut against, and the rib 711 extends along an extension direction of the guide groove 710. In this way, by providing the ribs 711, the contact area between the sliding protrusion 511 and the groove bottom of the guide groove 710 can be reduced, thereby reducing the energy loss in the process of the transducer module 500 sliding on the guide rail 700, thus making the transducer module 500 slide relatively smoothly.

In an embodiment, the guide rail 700 and the shell 400 are screw-locked. In this way, the position of the guide rail 700 relative to the shell 400 is relatively stable, thereby ensuring that the transducer module 500 can slide smoothly on the guide rail 700. However, the design is not limited to this, in other embodiments, the guide rail 700 and the shell 400 are interlocking connection.

In an embodiment, the guide rail 700 is provided with a guide groove 710, the transducer module 500 is provided with a sliding protrusion 511 that slidingly cooperates with the guide groove 710, the openings 712 at both ends of guide groove 710 are provided to be gradually expanded in a direction away from each other. In this way, it is convenient for the sliding protrusion 511 to slide into the guide groove 710 from the opening 712, which is conducive to saving time in assembling the ultrasonic treatment tip 300.

In an embodiment, the shell 400 is provided with a via hole 421 for the transmission mechanism 600 to pass through, and the transmission mechanism 600 covers the through hole 421. Without loss of generality, the receiving cavity 430 can be configured to receive the ultrasonic transmission medium, such as but not limited to water, in order to prevent water from flowing out of the receiving cavity 430 via the via hole 421 penetrated by the transmission structure, in this solution, the transmission mechanism 600 covers the via hole 421 to avoid water from leaking out. Specifically, the transmission mechanism 600 always covers the via hole 421 during the swing process.

In an embodiment, a hole wall of the via hole 421 is provided with a spherical arc surface, and the transmission mechanism 600 is provided with a covering portion forming a spherical pair with the spherical arc surface. It can be understood that the spherical pair has a relatively high degree of freedom, which makes it difficult for the covering portion and the via hole 421 to interfere during relative movement. However, the present design is not limited to this, in other embodiments, the hole wall of the via hole 421 is provided with a tile surface, an extension direction of the tile surface is consistent with a swing direction of the transmission mechanism 600, and the covering portion and the via hole 421 form a revolute pair.

In an embodiment, a first sealing ring 800 is provided between the via hole 421 and the transmission mechanism 600. It can be understood that, the transmission mechanism 600 can be movably connected to the hole wall surface of the via hole 421 via the first sealing ring 800, by providing the first sealing ring 800, the tightness of the receiving cavity 430 is improved to prevent the ultrasonic transmission medium from leaking out.

In an embodiment, the shell 400 includes a shell body 410 provided with a first port and the heat dissipation structure 420 covering the first port 610, the shell body 410 and the heat dissipation structure 420 are configured to limit the receiving cavity 430, and the transmission mechanism 600 is passed through the heat dissipation structure 420. It can be understood that the transducer module 500 will generate relatively great heat when working, thereby causing the temperature inside the receiving cavity 430 to be relatively high, by setting the heat dissipation structure 420, the relatively great heat can be dissipated from the receiving cavity 430, thereby making the temperature in the receiving cavity 430 relatively low, so that allows the ultrasonic treatment tip 300 to operate for a relatively long period of time. Without loss of generality, in an embodiment, the heat dissipation structure 420 is configured to connect the ultrasonic treatment handle 200, in this way, if the ultrasonic treatment handle 200 is provided with a heat dissipation system, the heat dissipation structure 420 can utilize the heat dissipation system of the treatment handle to export heat.

In an embodiment, the heat dissipation structure 420 is provided with an installation hole connected to the receiving cavity 430, and the ultrasonic treatment tip 300 further includes a buffer film assembly 910 provided at the installation hole, the buffer film assembly 910 is configured to balance the pressure changes in the receiving cavity 430. Specifically, the buffer film assembly 910 includes a buffer film sealing ring 930, a buffer film 920 and a buffer film cover plate 940, thus, when the buffer film 920 plays a buffering role, the sealing performance of the receiving cavity 430 is improved by the buffer film sealing ring 930, and the buffer film 920 is prevented from being damaged and causing rupture by the buffer film cover 940. Buffer film assembly 910 can be provided in two at intervals to enhance the ability of balancing pressure changes inside the receiving cavity 430.

The present application provides an ultrasonic therapeutic apparatus.

Referring to FIG. 17 to FIG. 30, in the embodiment according to the present application, the ultrasonic therapeutic apparatus includes a treatment tip 100, a transducer module 20, a handle 200 and a refrigeration unit 60. The treatment tip 100 includes a cover body 501 and a shell 400, the cover body 501 and the shell 400 are configured to limit a receiving cavity for receiving an ultrasonic transmission medium, and the cover body 501 is provided with a heat dissipation structure 420 in contact with the ultrasonic transmission medium; the transducer module 20 is provided at the receiving cavity; the handle 200 includes an outer shell 401 and an end cap 42, the outer shell 401 and the end cap 42 are configured to limit an installation cavity, and the end cap 42 is installed at the cover body 501 and is provided with a thermal conductive portion 43 thermally connected to the heat dissipation structure 420; the refrigeration unit 60 is provided at the installation cavity and thermally connected to the thermal conductive portion 43 to cool heat generated when the transducer module 20 is working, and the heat is transferred to the thermal conductive portion 43 via the ultrasonic transmission medium and the heat dissipation structure 420. Setting in this way, by utilizing the heat transfer cooperation between the heat dissipation structure 420 and the thermal conductive portion 43, the heat inside the treatment tip 100 is transferred to the handle 200, and cooling is performed by the refrigeration unit 60 to prevent the heat generated by the transducer module 20 from increasing the temperature of the receiving cavity and causing thermal burns to the patient, while improving the use security of the ultrasonic therapeutic apparatus, the heat dissipation efficiency of the treatment tip 100 is further improved, thereby ensuring the normal use of the transducer module 20, so as to achieve the purpose of treatment.

The cover body 501 and the shell 400 are connected to form a closed receiving cavity, which prevents the ultrasonic transmission medium from leaking out and ensures the normal propagation of ultrasonic waves. The ultrasonic transmission medium can be configured as, but is not limited to, water or silicone oil. The ultrasonic transmission medium at least covers the sound-emitting surface 22 of the transducer module 20 and the heat dissipation structure 420, in this way, while ensuring the normal propagation of ultrasonic waves, the generated heat can be transferred to the heat dissipation structure 420 via the ultrasonic transmission medium and then be discharged from the treatment tip 100 to reduce the temperature inside the receiving cavity, thereby, the use security of the ultrasonic therapeutic apparatus is improved while improving the heat dissipation efficiency of the treatment tip 100. Furthermore, outside the shell cover is sleeved with a protective shell, which can not only protect the shell 400, but also prevent the shell 400 with relatively high temperature from coming into contact with the human body.

The end cap 42 and the cover body 501 can be connected and fixed by detachable connection methods such as buckling, screwing or the like, thereby facilitating the mutual disassembly and assembly of the treatment tip 100 and the handle 200, which is beneficial to separate processing and manufacturing and improvement of the maintenance convenience.

When the end cap 42 is installed at the cover body 501, the heat dissipation structure 420 can conduct heat transfer with the thermal conductive portion 43 of the end cap 42, that is, the heat inside the treatment tip 100 can be transferred to the handle 200 via the heat dissipation structure 420, and by the heat transfer cooperation between the thermal conductive portion 43 and the refrigeration unit 60 in the handle 200, the heat transfer speed in the treatment tip 100 is further accelerated and the heat dissipation efficiency of the treatment tip 100 is improved.

The setting of the refrigeration unit 60 can cool the thermal conductive portion 43, the refrigeration unit 60 can be in direct contact with the thermal conductive portion 43, or can be connected via a thermal conductive material such as thermal silicone grease, so that the thermal conductive portion 43 can efficiently absorb the heat transferred by the heat dissipation structure 420, thereby further speeding up the heat dissipation efficiency of the heat dissipation structure 420, lowering the temperature inside the receiving cavity, and it is conducive to preventing the situation that the temperature of the treatment tip 100 is too high to cause thermal burns to the human body from happening.

Both the thermal conductive portion 43 and the heat dissipation structure 420 can be made of materials with relatively good thermal conductivity such as aluminum, copper and so on, the heat dissipation structure 420 is at least partially exposed at the surface of the cover body 501 facing the end cap 42, and the thermal conductive portion 43 can be an integral part of the end cap 42; or, the end cap 42 is entirely composed of a thermal conductive portion 43, so as to ensure efficient heat transfer performance of the thermal conductive portion 43 as an intermediate medium for heat transfer between the heat dissipation structure 420 and the refrigeration unit 60, and the reliability of the heat transfer connection between the heat dissipation structure 420 and the thermal conductive portion 43, thereby achieving the heat dissipation purpose of the treatment tip 100.

In the technical solution of the present application, the heat transfer cooperation between the heat dissipation structure 420 and the thermal conductive portion 43 is utilized to transfer the heat inside the treatment tip 100 to the handle 200 and perform cooling by the refrigeration unit 60, thereby preventing the heat generated by the transducer module 20 from raising the temperature of the receiving cavity and causing thermal burns to the patient, the heat dissipation efficiency of the treatment tip 100 is further improved while improving the use security of the ultrasonic therapeutic apparatus, ensuring that the ultrasonic waves of the transducer module 20 are normally emitted and focused on the treatment area of the patient, thereby achieving the purpose of treatment.

Figure 17:
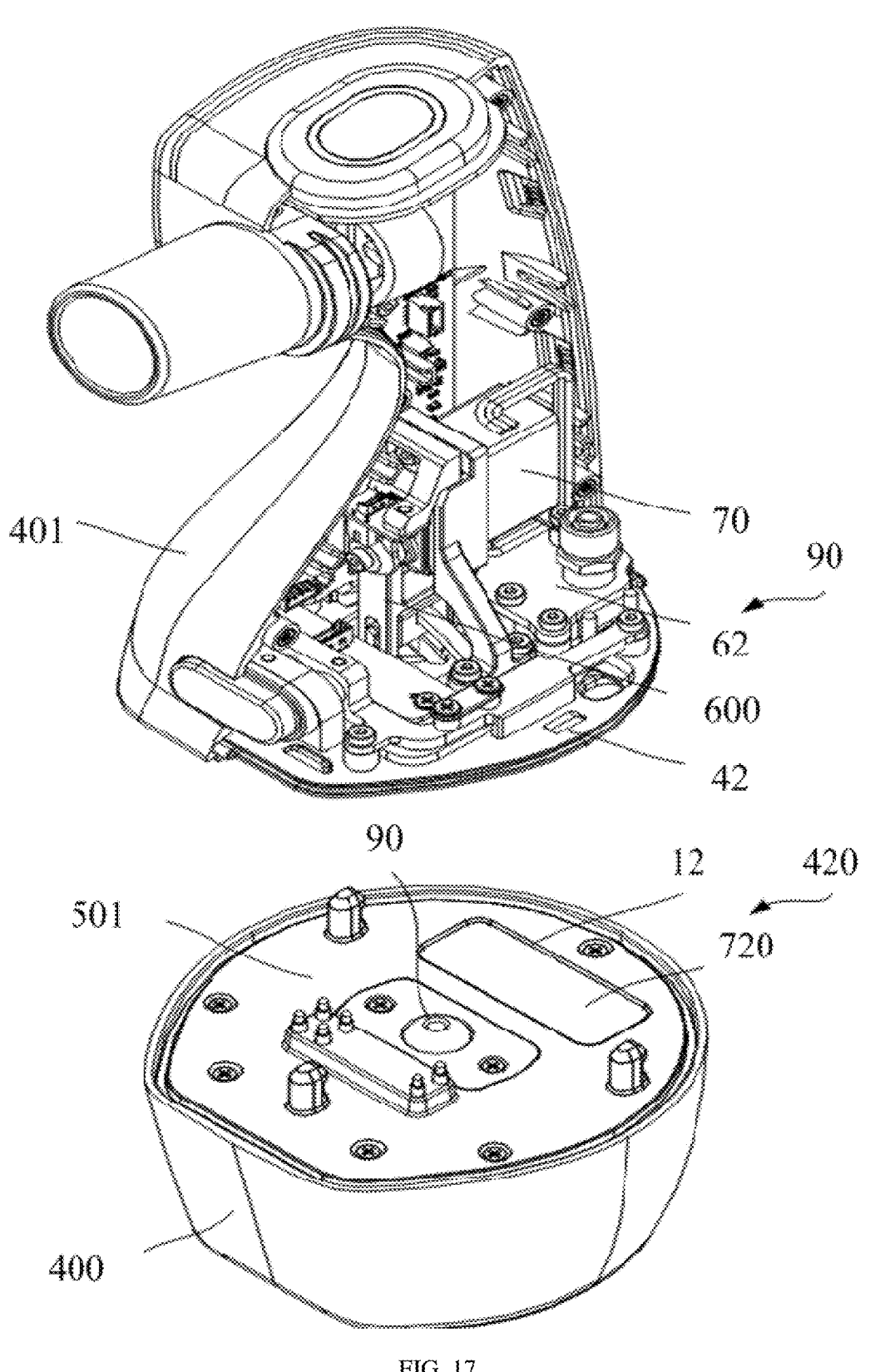
FIG. 17 is an exploded view of the ultrasonic therapeutic apparatus in FIG. 1.
Figure 18:
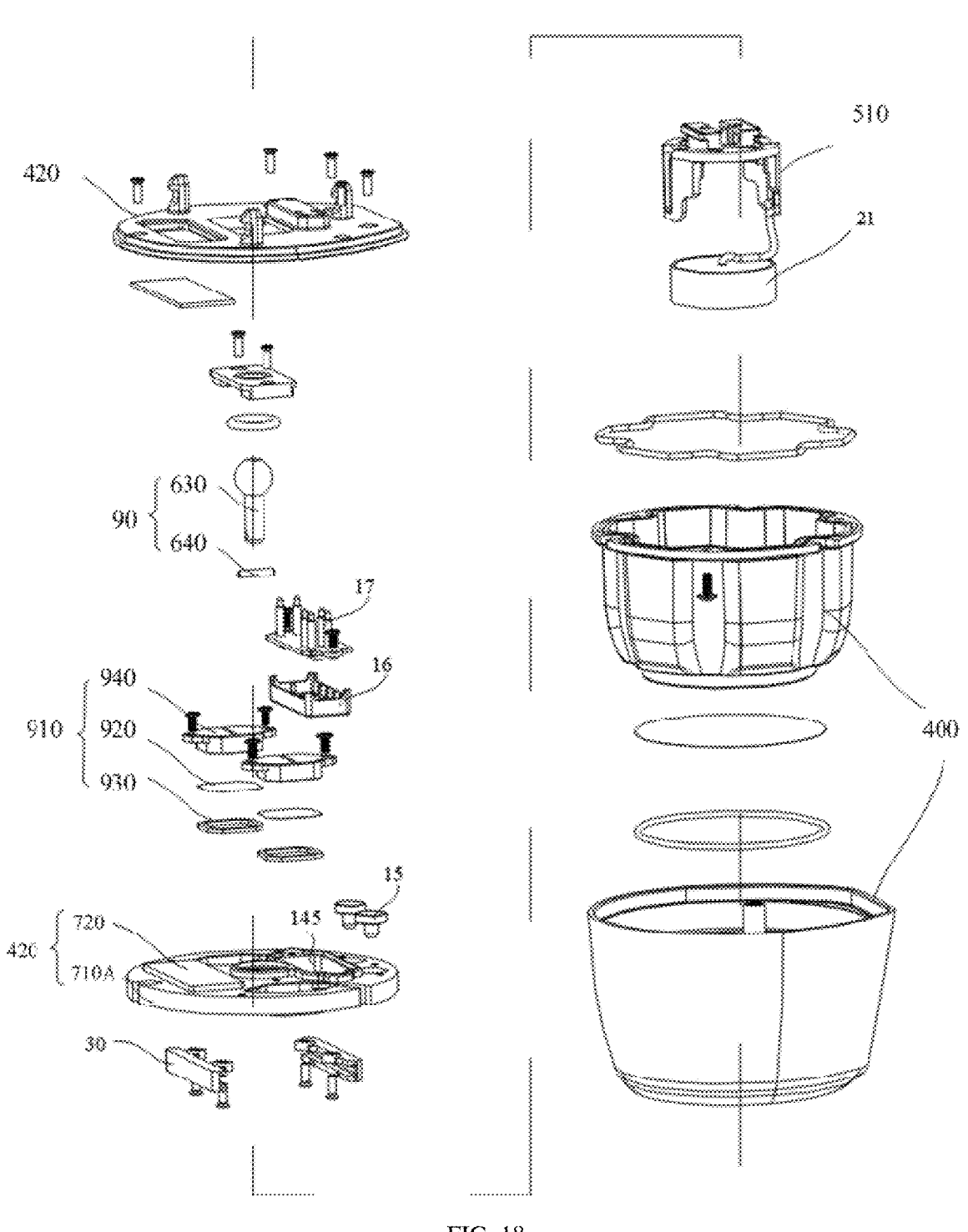
FIG. 18 is an exploded view of a treatment tip.
Figure 19:
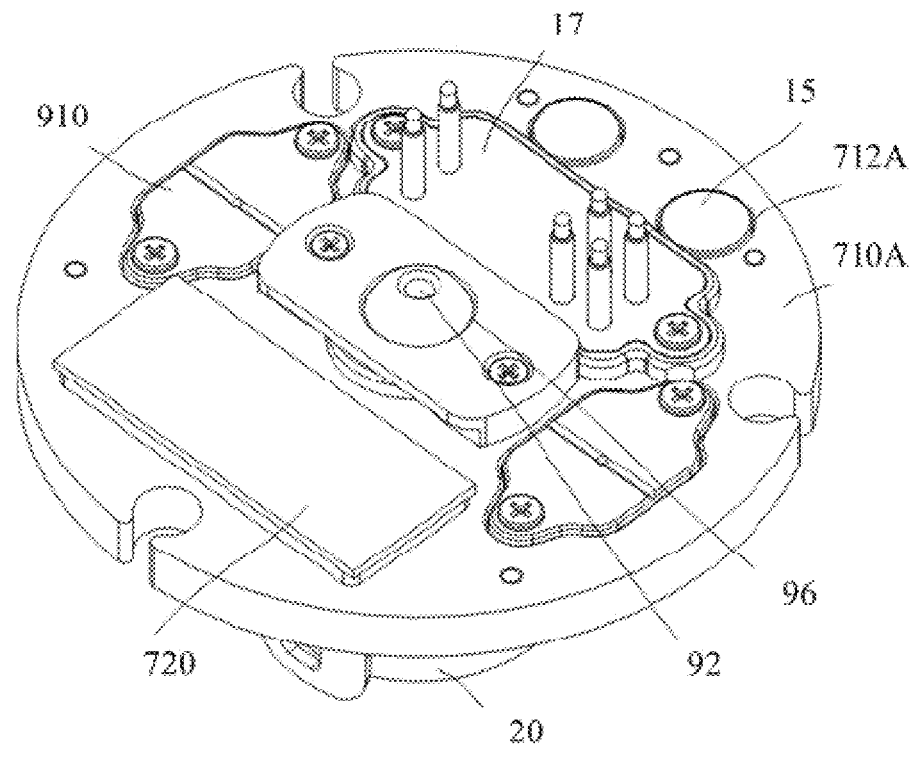
FIG. 19 is a structural schematic view of the heat dissipation structure.

Referring to FIG. 17 to FIG. 19, in an embodiment, the cover body 501 is provided with an avoidance opening 12, the heat dissipation structure 420 includes a heat dissipation main body 710A and a first heat dissipation convex portion 720 connected to one side of the heat dissipation main body 710A, and the first heat dissipation convex portion 720 is configured to pass through the avoidance opening 12 and thermally connect to the thermal conductive portion 43. Setting in this way, the thermal conductivity efficiency between the thermal conductive portion 43 and the heat dissipation structure 420 is improved while facilitating the rapid assembly of the heat dissipation structure 420 to the cover body 501.

The shape and structure of the heat dissipation main body 710A is similar to the cover body 501, which is conducive to increasing the contact area with the ultrasonic transmission medium, the setting of the first heat dissipation convex portion 720 can not only be accurately aligned with the avoidance opening 12 to facilitate assembly, but also enable efficient heat transfer between the heat dissipation main body 710A and the thermal conductive portion 43 to improve the heat dissipation efficiency of the treatment tip 100.

In an embodiment, the heat dissipation structure 420 further includes a second heat dissipation convex portion connected to another side of the heat dissipation main body 710A, and the second heat dissipation convex portion is configured to perform heat transferring with the ultrasonic transmission medium. Thus, it is conducive to further increasing the effective contact area between the heat dissipation structure 420 and the ultrasonic transmission medium, thereby allowing a large amount of heat to be conducted to the thermal conductive portion 43 via the heat dissipation structure 420. The second heat dissipation convex portion may be provided with multiple, and they are arranged on the other side of the heat dissipation main body 710A to enhance the heat dissipation effect.

In an embodiment, the heat dissipation main body 710A is provided with a wire via hole 711A for a wire harness of the transducer module 20 to pass through and a caulking groove 145 connected to the wire via hole 711A, and the caulking groove 145 is provided away from the first heat dissipation convex portion 720; the treatment tip 100 further includes a insulating shell 16 and a circuit adapter board 17 that are fixedly connected, and the insulating shell 16 is adapted to the caulking groove 145 and provided with a through hole connected to the wire via hole 711A; the circuit adapter board 17 is fixedly connected to an edge of the caulking groove 145, and a first plugging element is provided between the wire harness of the transducer module 20 and the through hole. In this way, the heat dissipation structure 420 not only undertakes the heat dissipation function, but also undertakes the wire passing function, which enriches the functions of the heat dissipation structure 420, and can avoid opening the wire via hole on the shell 400, which is helpful for the shell 400 to maintain structural integrity, so that the shell 400 has relatively high structural strength.

The caulking groove 145 provided on the heat dissipation main body 710A is provided away from the first heat dissipation convex portion 720, which is beneficial for the circuit adapter board 17 to being away from the first heat dissipation convex portion 720, thereby preventing the ambient temperature around the circuit adapter board 17 from being too high to cause that the circuit adapter board 17 can not work properly. Secondly, utilizing the insulating shell 16 to match the structure of the caulking groove 145 and embed the caulking groove 145, the circuit adapter board 17 is fixedly connected to the insulating shell 16 and fixed with the heat dissipation main body 710A, which can enhance the assembly stability, at the same time, the wire harness can pass through the through hole on the insulating shell 16 to achieve electrical connection with the circuit adapter element 17, which can further improve the reliability of the electrical connection between the wire harness and the circuit adapter board 17. After the wire harness passes through the through hole, there exists a gap between the wire harness and the hole wall of the through hole. In order to avoid the leakage of the ultrasonic transmission medium, a first plugging element is provided between the wire harness and the through hole, so that the tightness of the receiving cavity is relatively high.

Referring to FIG. 19, in an embodiment, the heat dissipation main body 710A is provided with an ultrasonic transmission medium via the hole 712A, the ultrasonic transmission medium via the hole 712A is provided along a circumferentia of the heat dissipation main body 710A, and the treatment tip 100 further includes a second plugging element 15 provided at the ultrasonic transmission medium via the hole 712A. In this way, the heat dissipation structure 420 not only undertakes the heat dissipation function, but also undertakes the function of introducing the ultrasonic transmission medium into the receiving cavity 430, which enriches the functions of the heat dissipation structure 420, and can avoid opening the ultrasonic transmission medium via the hole 712A on the shell 400, which is helpful for the shell 400 to maintain structural integrity, so that the shell 400 has relatively high structural strength.

The ultrasonic transmission medium via the hole 712A is provided along the circumference of the heat dissipation main body 710A. It is understandable that the idle area on the heat dissipation main body 710A can be utilized to create an ultrasonic transmission medium via the hole 712A, which does not affect the normal assembly and use of other components, but also allows the ultrasonic transmission medium to be smoothly introduced into the receiving cavity without directly impacting the transducer module 20. After the ultrasonic transmission medium is introduced into the receiving cavity, the ultrasonic transmission medium via the hole 712A is blocked by the second plugging element 15 to avoid leakage of the ultrasonic transmission medium.

When the second plugging element 15 is made of silicone, rubber or other materials, the ultrasonic transmission medium via the hole 712A is provided away from the first heat dissipation convex portion 720, which can also prevent the second plugging element 15 from softening and catalyzing due to excessive high ambient temperature. Setting in this way can further improve the service life and sealing effect of the second plugging element 15.

Referring to FIG. 18 and FIG. 19, in an embodiment, the heat dissipation main body 710A is provided with a buffer film assembly 910, and the buffer film assembly 910 is configured to balance a pressure change in the receiving cavity. It can be understood that the heat dissipation main body 710A is provided with an installation hole, the buffer film assembly 910 is provided at the installation hole, the buffer film assembly 910 includes a buffer film sealing ring 930, a buffer film 920 and a buffer film cover plate 940, thus, when the buffer film 920 plays a buffering role, the sealing performance of the receiving cavity 430 is improved by the buffer film sealing ring 930, and the buffer film 920 is prevented from being damaged and causing rupture by the buffer film cover 940. Buffer film assembly 910 can be provided in two at intervals to enhance the ability of balancing pressure changes inside the receiving cavity.

Specifically, the heat generated when the transducer module 20 is working will heat the ultrasonic transmission medium, thus causing the ultrasonic transmission medium to expand due to heat, the sound-permeable membrane in the treatment tip 100 will be damaged in severe cases, causing the treatment tip 100 to fail to work properly, therefore, setting up the buffer film assembly 910 can prevent the pressure in the receiving cavity from acting concentratedly on the sound-permeable membrane and causing damage to the sound-permeable membrane, thereby prolonging the service life of the treatment tip 100, and improving the use security of the treatment tip 100 and the effectiveness of ultrasonic treatment. Certainly, in other embodiments, the buffer film assembly 910 can be integrated into the first plugging element to reduce the number of through-hole opened in the heat dissipation main body 710A, so that the heat dissipation main body 710A has relatively high structural strength.

Figure 25:
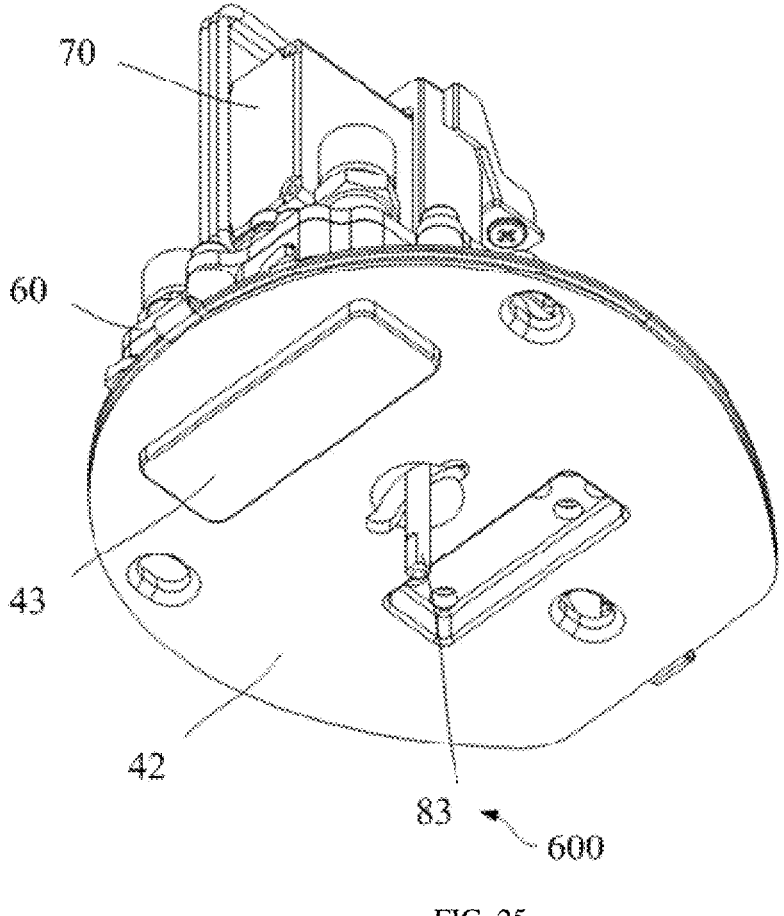
FIG. 25 is a structural schematic view of a thermal conductive portion.

Referring to FIG. 25, in an embodiment, the thermal conductive portion 43 is protruding from a side of the end cap 42 facing the cover body 501 and provided to extend toward the avoidance opening 12. Thus, it is advantageous for the thermal conductive portion 43 to be inserted into the avoidance opening 12 to achieve reliable and rapid assembly of the handle 200 and the treatment tip 100. Moreover, the thermal conductive portion 43 can be brought as close as possible to the first heat dissipation convex portion 720 of the heat dissipation main body 710A, thereby improving the heat transfer reliability and heat transfer efficiency of the thermal conductive portion 43 and the heat dissipation structure 420.

Referring to FIG. 17 and FIG. 24 to FIG. 27, in an embodiment, the refrigeration unit 60 includes a semiconductor refrigeration assembly 61, the semiconductor refrigeration assembly 61 includes a semiconductor refrigeration piece 611, a refrigeration piece cold plate 613 and a refrigeration piece hot plate, and the semiconductor refrigeration piece 611 is provided with an external power supply conducting wire 612; one side of the refrigeration piece cold plate 613 is attached to a cold end of the semiconductor refrigeration piece 611, and another side of the refrigeration piece cold plate 613 is attached to the thermal conductive portion 43; the refrigeration piece hot plate is attached to a hot end of the semiconductor refrigeration piece 611 to cool the hot end. Thus, it can speed up the heat dissipation efficiency of the thermal conductive portion 43.

Specifically, the refrigeration piece hot plate and the refrigeration piece cold plate 613 overlap each other, the two sides facing each other of the refrigeration piece hot plate and the refrigeration piece cold plate 613 are clamped together and fixed with a thermal insulation pad 614, and are enclosed with the heat insulation pad 614 to form a clamping cavity for the installation of the semiconductor refrigeration piece 611, thereby preventing the spread of heat, and making the semiconductor refrigeration piece 611 conduct electricity normally and cool the thermal conductive portion 43 to dissipate heat.

The principle is the same as that of the semiconductor refrigeration piece 611 in the prior art, which realizes the movement of electrons by conducting electricity on the interconnected N-type semiconductor and P-type semiconductor, thus, heat is generated under the action of the semiconductor's own resistance, and the heat is transferred from one end to another end, resulting in a temperature difference to form a cold end and a hot end. In this embodiment, the hot end of the semiconductor refrigeration piece 611 that generates heat is installed correspondingly with the refrigeration piece hot plate, when the hot end generates heat, it can conduct heat to the refrigeration piece hot plate to cool the hot end, further reducing the temperature of the cold end to achieve better cooling effect. One side of the thermal conductive portion 43, and another side of the refrigeration piece cold plate 613 is attached to the cold end of the semiconductor refrigeration piece 611, due to the temperature loss of the hot end, according to the temperature balance characteristics of the semiconductor refrigeration piece 611, the low temperature generated by the cold end will also be further reduced, thereby achieving a better cooling effect on the thermal conductive portion 43. Therefore, by the setting of the semiconductor refrigeration assembly 61, the heat dissipation efficiency of the thermal conductive portion 43 can be further accelerated. Moreover, the semiconductor refrigeration piece 611 has a compact structure and flexible assembly, which can be apply to cool heating components with different temperature requirements, thereby increasing the application breadth.

Figure 27:
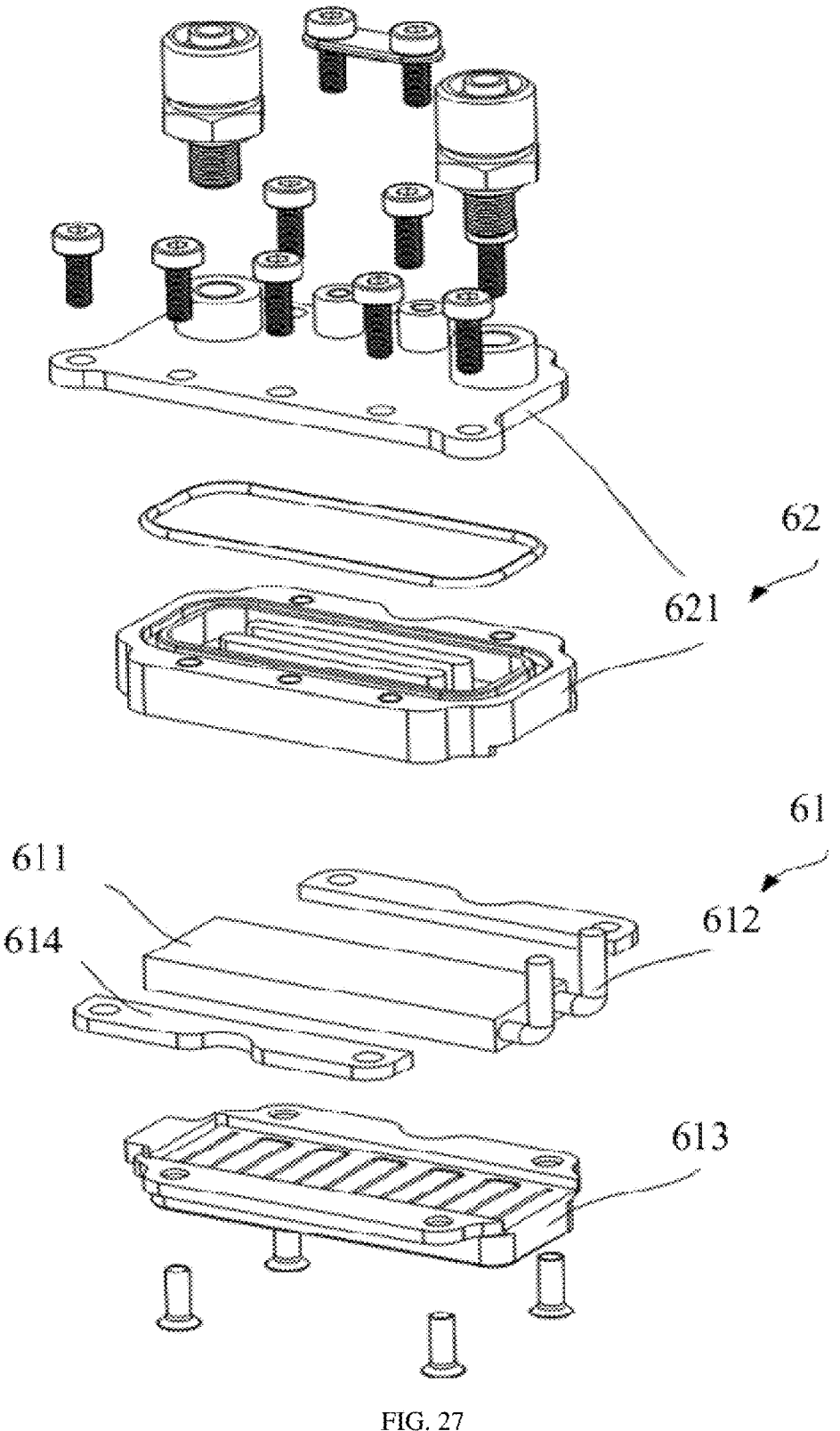
FIG. 27 is an exploded view of a semiconductor refrigeration assembly and a water cooling assembly.

Referring to FIG. 27, in an embodiment, the refrigeration unit 60 includes a water cooling assembly 62, and the water cooling assembly 62 includes a water tank 621; the water tank 621 is thermally connected to the thermal conductive portion 43, and the water tank 621 is provided with coolants for heat exchange. Setting in this way, utilizing the coolant to achieve heat exchange with the thermal conductive portion 43 can further accelerate the heat dissipation efficiency of the thermal conductive portion 43.

Specifically, the water tank 621 can be directly attached to and abutted against the thermal conductive portion 43, which can accelerate the heat dissipation efficiency of the thermal conductive portion 43 by the coolant. Furthermore, the semiconductor refrigeration assembly 61 and the water cooling assembly 62 can be integrated into one, for example, the refrigeration piece hot plate and the water tank 621 are provided to be integrated, that is, a flowing cavity is set up inside the refrigeration piece hot plate, and the coolant is placed inside the flowing cavity. By allowing the coolant to flow inside the flowing cavity, it is conducive to further increasing the heat dissipation speed of the hot end, thus reducing the extreme temperature of the cold end. At the same time, the structure is compact, the number of parts are reduced and the space occupied is reduced.

Figure 28:
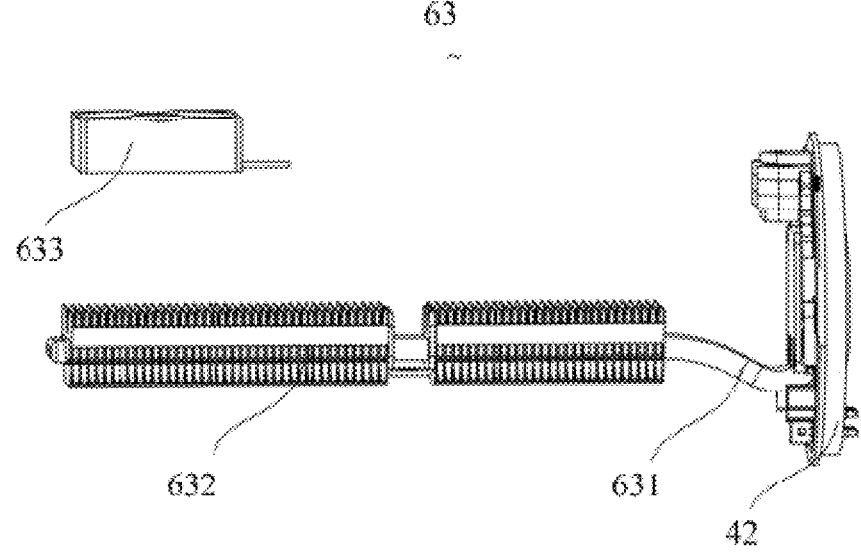
FIG. 28 is an exploded view of an air-cooled assembly.

Referring to FIG. 28, in an embodiment, the refrigeration unit 60 includes an air-cooled assembly 63, and the air-cooled assembly 63 includes a heat pipe 631, a fin 632 and a fan 633; a heat-absorbing end of the heat pipe 631 is thermally connected to the thermal conductive portion 43, a heat dissipation end of the heat pipe 631 is provided with the fin 632, and the fan 633 is configured to make outside air exchange heat with the heat dissipation end of the heat pipe 631 and the fin 632. Setting in this way, utilizing the cooperation of the heat pipe 631, fin 632 and fan 633 to achieve heat exchange with the thermal conductive portion 43 to an extremely great extent, the heat dissipation efficiency of the thermal conductive portion 43 can be further accelerated.

Specifically, a plurality of fins 632 can be provided, and the fins are provided at intervals at the heat dissipation end of the heat pipe 631, and the air outlet of the fan 633 can be provided toward the heat dissipation end, so that the heat dissipation area can be increased by the setting of heat pipe 631 and fins 632, and at the same time, the pressure difference formed when the fan 633 is working can be utilized, and the external air flows into the handle 200 to form an air flow, so that the heat from the heat dissipation end of the heat pipe 631 and the heat from the fin 632 are all dissipated to the outside of the handle 200 along with the air flow to prevent hot air from gathering inside the handle 200 and affecting the normal use of other parts, so as to achieve heat dissipation requirements. Certainly, in other embodiments, the air-cooled assembly 63 may also include a fin 632 and a fan 633, the fin 632 is thermally connected to the thermal conductive portion 43, which can also increase the heat dissipation area and improve the heat dissipation efficiency of the thermal conductive portion 43.

In an embodiment, the semiconductor refrigeration assembly 61 and the air-cooled assembly 63 are integrated into one, for example, the heat-absorbing end of the heat pipe 631 and the refrigeration piece hot plate are provided to be integrated, and the heat dissipation end of the heat pipe 631 is provided with fins 632, thus can further increase the effective contact area with the air, thereby further improving the heat dissipation efficiency of the hot end, and thereby reducing the extreme temperature of the cold end.

In another embodiment, the water cooling assembly 62 and the air-cooled assembly 63 are integrated into one, for example, the heat-absorbing end of the heat pipe 631 and the refrigeration piece hot plate are provided to be integrated, the heat dissipation end of the heat pipe 631 is provided with fin 632 and connected to the water tank 621, thus can further increase the effective contact area with the air and the heat exchange effect with the coolant, thereby further improving the heat dissipation efficiency of the hot end, and thereby reducing the extreme temperature of the cold end.

In yet another embodiment, the semiconductor refrigeration assembly 61, the water cooling assembly 62 and the air-cooled assembly 63 are integrated into one, which can greatly improve the heat dissipation efficiency of the thermal conductive portion 43, thereby improving the heat dissipation efficiency of the treatment tip 100.

Figure 24:
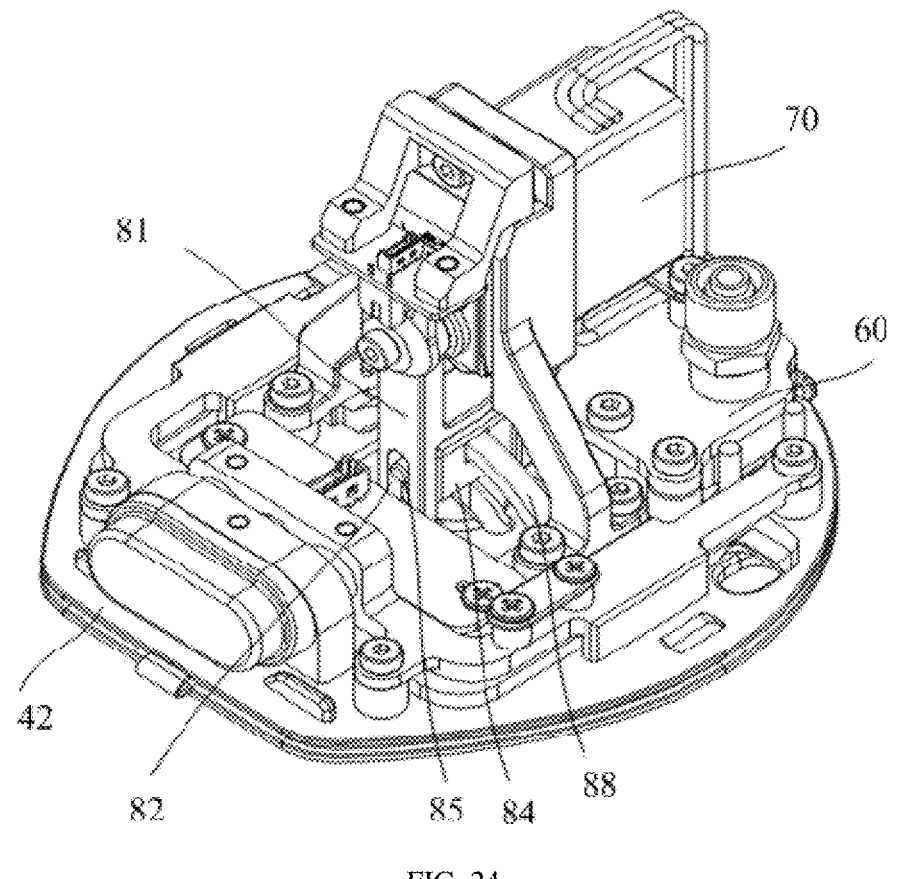
FIG. 24 is an assembly schematic view of a refrigeration unit, a driving member and a transmission mechanism.
Figure 26:
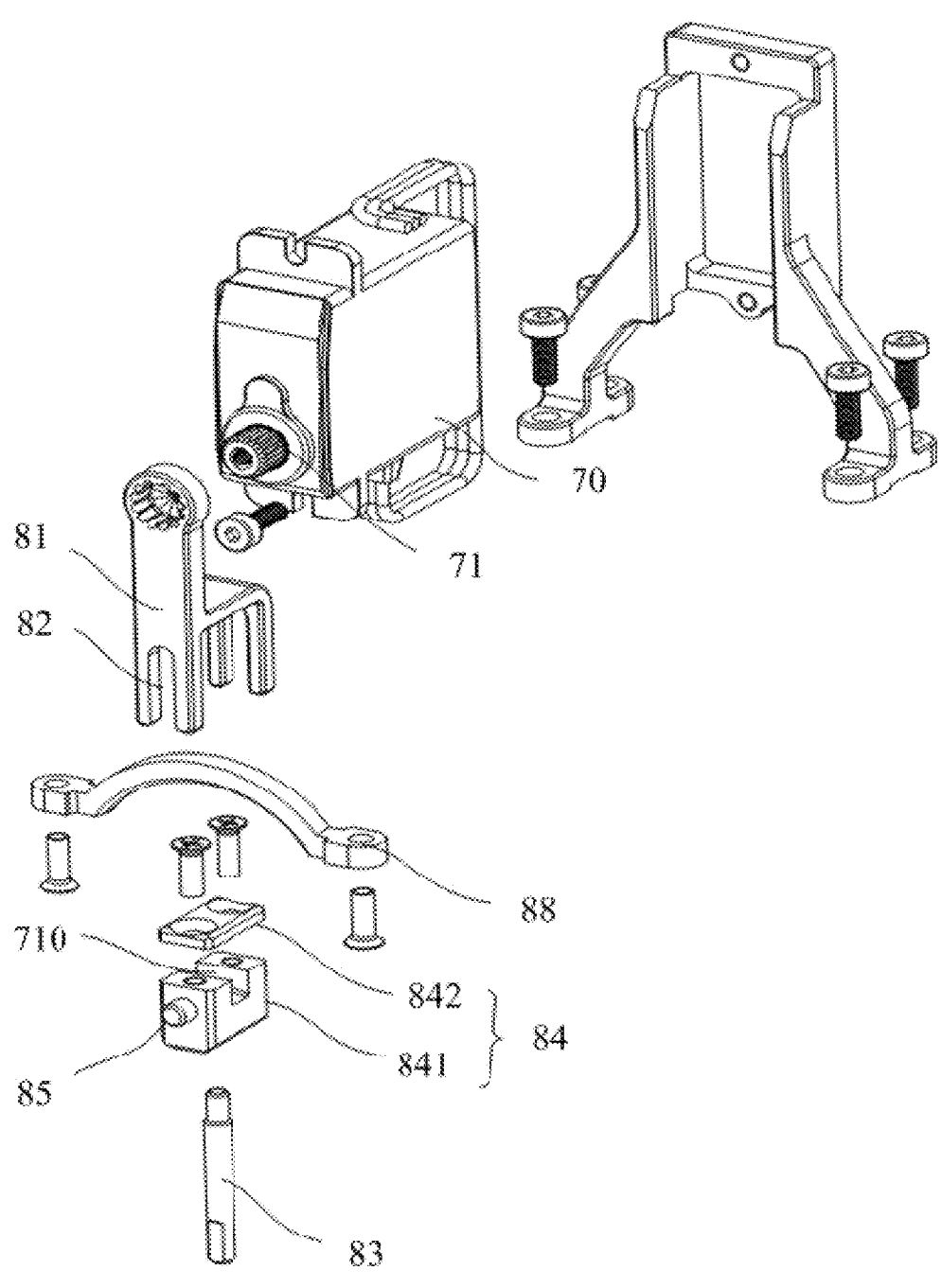
FIG. 26 is an exploded view of the driving member and the transmission mechanism.

Referring to FIG. 24 to FIG. 26, in an embodiment, the ultrasonic therapeutic apparatus further includes a driving member 900 and a transmission assembly, the driving member 900 is provided at the installation cavity, the transmission assembly includes a transmission mechanism 600 and a linkage mechanism 90, the transmission mechanism 600 is transmission connected to the driving member 900, the linkage mechanism 90 is rotatably passed through the cover body 501 and provided with a first end 610 and a second end 620, the first end 610 is drivingly connected to the transmission mechanism 600, the second end 620 is transmission connected to the transducer module 20 to drive the transducer module 20 to perform reciprocating motion. In this way, the focusing area of the ultrasonic waves emitted by the transducer module 20 can be broadened, and then, for the treatment area of the same area, the operator can reduce the number of times of moving the ultrasonic therapeutic apparatus, thereby reducing the operator's workload.

The transmission mechanism 600 and the linkage mechanism 90 are respectively located inside the handle 200 and the treatment tip 100, which facilitates the replacement of the handle 200 or the treatment tip 100 individually and improves the versatility of the handle 200 and the treatment tip 100.

The first end 610 is drivingly connected to the transmission mechanism 600, and is rotatably passed through the cover body 501, so as to facilitate the first end 610 to drive the transducer module 20 connected to the second end 620 to swing in the treatment tip 100 under the drive of the transmission mechanism 600, thereby achieving the purpose of widening the focusing area of the ultrasonic waves emitted by the transducer module 20.

Figure 29:
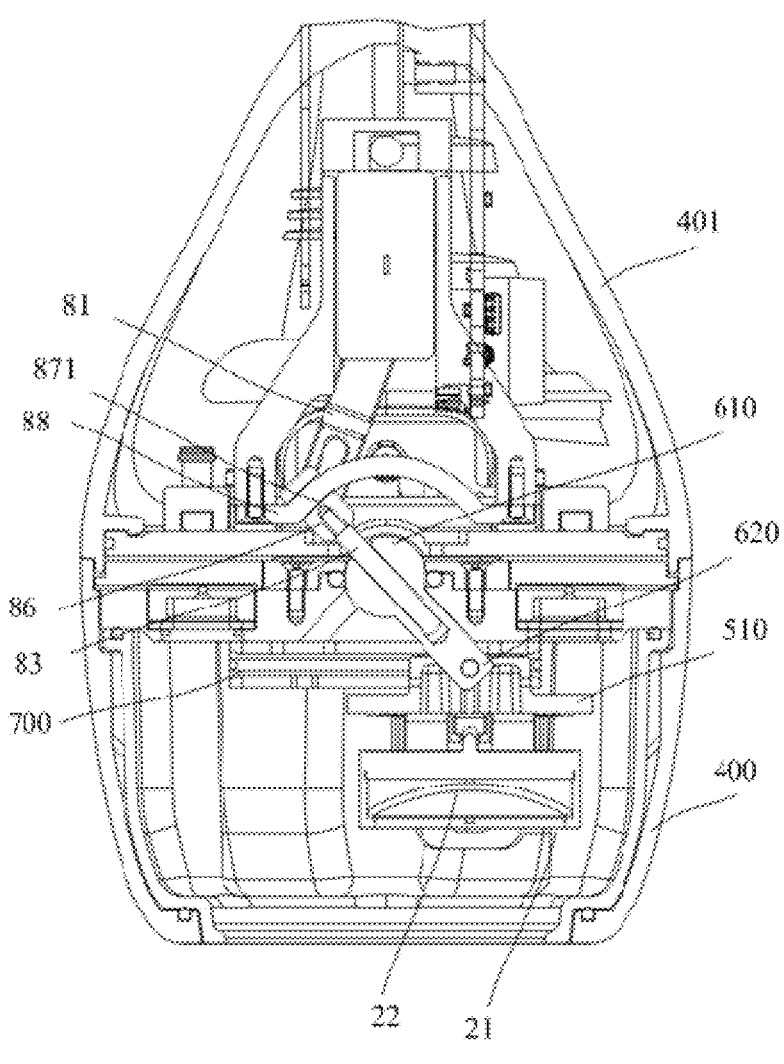
FIG. 29 is a section view of the ultrasonic therapeutic apparatus when the transducer module is on the right side.
Figure 30:
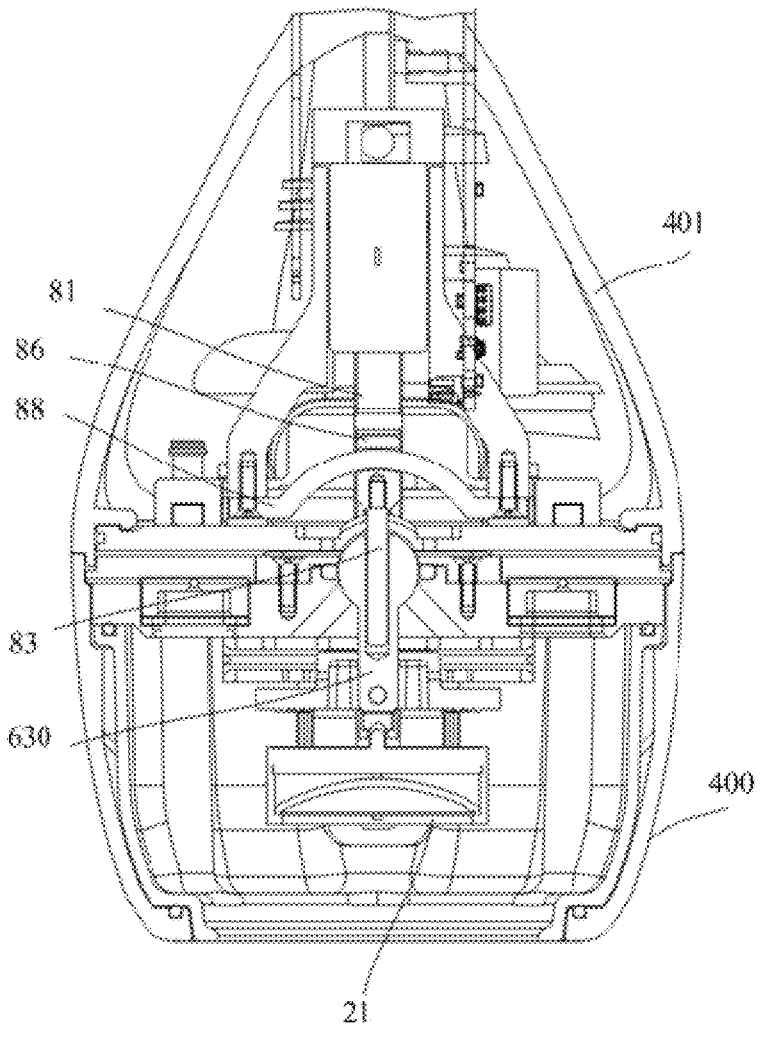
FIG. 30 is a section view of the ultrasonic therapeutic apparatus when the transducer module is in the central part.

With reference to FIG. 26, FIG. 28 and FIG. 29, in an embodiment, the driving member 900 includes a drive shaft 71, the transmission mechanism 600 includes a swing bracket 81 and a swing member 83, one end of the swing bracket 81 is fixedly connected to the drive shaft 71, and another end of the swing bracket 81 is transmission connected to the swing member 83, and the first end 610 is provided with a buffer drill way 92 for the swing member 83 to be inserted and slidably passed through. It can be understood that the driving member 900 is a motor, and the driving shaft 71 is driven by the forward rotation and reverse rotation of the motor to cause the swing bracket 81 connected to the driving shaft 71 to swing back and forth, thereby causing the swing member 83 to swing accordingly, thereby driving the transducer module 20 to perform reciprocating motion by the linkage mechanism 90.

Specifically, the swing bracket 81 and the drive shaft 71 can be connected and fixed via a mortise and tenon structure, a spline structure or the like, which facilitates disassembly and assembly, and at the same time, the swing bracket 81 and the drive shaft 71 can restrict each other to prevent relative movement between the swing bracket 81 and the drive shaft 71, thereby ensuring the transmission effectiveness and transmission reliability between the drive shaft 71 and the swing bracket 81.

The swing bracket 81 is transmission connected to the swing member 83, which can be transmitted connection by the means of a transfer structure, hinges or the like, so as to avoid the direct connection between the swing bracket 81 and the swing member 83, which may cause structural breakage during movement.

The swing member 83 is insertable and slidably passes through the buffer drill way 92 of the first end 610, when the swing member 83 swings driven by the swing bracket 81, the first end 610 moves accordingly and drives the transducer module 20 connected to the second end 620 to swing accordingly. The swing member 83 can be a rod-shaped structure, one end of the swing member 83 is transmission connected to the swing bracket 81, and the end cap 42 is provided with a connection via hole, another end of the swing member 83 can be extended and inserted into the buffer drill way 92 via the connection via hole, on the one hand, it can increase the contact area with the first end 610, and improve the reliability of transmission, on the other hand, slidingly connecting to the buffer drill way 92, that is, a movable gap is provided between the buffer drill way 92 and the swinging member 83, can provide buffering for the transmission between the swinging member 83 and the linkage mechanism 90, prevent motion interference between the swinging member 83 and the linkage mechanism 90, so that the swinging member 83 can reliably drive the transducer module 20 to perform reciprocating motion via the linkage mechanism 90.

Referring to FIG. 26, in an embodiment, the transmission mechanism 600 further includes a slidingly connected adapter 84 and a guide frame 88, the adapter 84 is slidably and rotatably connected to the swing bracket 81, the adapter 84 is fixedly connected with the swinging member 83, the guide frame 88 is passed through the adapter 84 to make the adapter 84 slide along the set path. In this way, the swing member 83 can swing along the set movement path while improving the transmission reliability of the swing bracket 81, thereby meeting the movement requirements of the transducer module 20.

Specifically, the adapter 84 serves as a transition part between the swing bracket 81 and the swing member 83. On the one hand, it can assist the connection between the swing member 83 and the swing bracket 81, effectively reducing the risk of structural breakage caused by the direct connection between the swing member 83 and the swing bracket 81, increasing the effective contact area between the swing member 83 and the swing bracket 81, and improving the connection stability and connection reliability between the swing member 83 and the swing bracket 81; on the other hand, by the slidable and rotatable connection and cooperation between the adapter 84 and the swing bracket 81 as well as the guiding function of the guide frame 88, the movement trajectory of the swing member 83 can be further limited reliably and effectively, and the movement reliability of the swing member 83 is improved.

The guide frame 88 is passed through the adapter 84, which enables the adapter 84 to reliably slide along the guide frame 88, thereby driving the swing member 83 connected to the adapter 84 to swing. And driving the transducer module 20 to reciprocate by the linkage mechanism 90 can also prevent the adapter 84 with the swing member 83 from detaching from the swing bracket 81 and causing transmission failure, thereby improving the transmission reliability of the swing bracket 81.

In an embodiment, the end of the swing bracket 81 away from the drive shaft 71 is provided with a limiting slot 82 extending along the direction of the swing bracket 81, and the adapter 84 is provided with a limit shaft 85 slidably and rotatably passed through the limit slot 82; in order to cooperate with the swing drive of the swing bracket 81, the swing member 83 is moved along the guide frame 88 via the adapter 84 to meet the movement requirements of the transducer module 2011.

Specifically, the limiting slot 82 extends and protrudes along the direction of the swing bracket 81 away from the drive shaft 71, and along the swing direction of the swing bracket 81, two limiting bumps provided at intervals are enclosed with the end of the swing bracket 81 to form the limiting slot 82. Two limiting slots 82 are provided at intervals, the adapter 84 is embedded between the two limiting slots 82, and is respectively clamped in the corresponding limiting slot 82 by the two limiting shafts 85, so that it can meet the swing requirements of the swing member 83.

On the one hand, increasing the contact area between the adapter 84 and the swing bracket 81, while the structure is more compact, not only can the adapter 84 be more firmly installed in the limiting slot 82 of the swing bracket 81, thereby enhancing connection stability and connection reliability, but it can also improve the transmission efficiency between the swing bracket 81 and the adapter 84. On the other hand, the swing bracket 81 swings driven by the driving shaft 71, the adapter 84 swings accordingly and can rotate relative to the limiting slot 82 by the limiting shaft 85, thereby driving the swing member 83 to move.

Referring to FIG. 28, in an embodiment, a threaded hole 86 is provided inside the adapter 84, and one end of the swing member 83 is threadedly connected to the threaded hole 86; its structure is simple, the connection is reliable, it is easy to disassemble and assemble, and it can improve the connection firmness and disassembly and assembly efficiency between the adapter 84 and the swing member 83. Certainly, the application is not limited to this, in other embodiments, the adapter 84 and the swinging member 83 can be relatively fixed via mortise and tenon, twist buckle, welding and other connection methods.

Referring to FIG. 26, in an embodiment, the adapter 84 includes a base 841 and a pressure plate 842, the base 841 is provided with a guide groove 710 on one side away from the swing member 83, the pressure plate 842 is detachably connected to the base 841 to cover the guide groove 710, and the guide frame 88 passes through the guide groove 710. The pressure plate 842 is covered on the base 841 by detachable connection methods such as bolting, embedding, snapping or the like, which can be further restrict the installation of the guide frame 88 inside the guide groove 71046 while facilitating the assembly of the guide frame 88.

In an embodiment, the groove bottom wall of the guide groove 710 is an arc-shaped structure 871 protruding toward a direction of the pressure plate 842; and/or, the guide frame 88 is an arch bridge structure, the arc-shaped structure 871 is adapted to the arch bridge structure, that is, the arc-shaped structure 871 is always attached to the arch bridge structure, which is conducive to the reliable sliding of the adapter 84 along the guide frame 88, which effectively prevents the adapter 84 from shaking on the guide frame 88 and ensures the consistency of the movement direction of the adapter 84, so that the swing member 83 swings along the set path, thereby meeting the movement requirements of the transducer module 2011.

In an embodiment, the driving member 900, the transmission mechanism 600, the end cap 42 and the cavity wall of the installation cavity jointly limit the assembly space, the refrigeration unit 60 is provided at the assembly space and is located above the thermal conductive portion 43. It can be understood that, the thermal conductive portion 43 is protruding from the side of the end cap 42 facing the cover body 501 and is provided to be extended toward the avoidance opening 12, it is convenient for the thermal conductive portion 43 to be inserted into the avoidance opening 12 and as close as possible to the first heat dissipation convex portion 720 of the heat dissipation main body 710A, and then, the heat of the first heat dissipation convex portion 720 is transferred to the other side of the end cap 42 away from the first heat dissipation convex portion 720 via the thermal conductive portion 43.

The transmission mechanism 600 is rotationally connected to the driving member 900 by the swing bracket 81, and extends out of the end cap 42 and inserts into the buffer drill way 92 inside the first end 610 by the swing member 83, in this way, it is conducive to utilizing the driving member 900, the transmission mechanism 600, the end cap 42 and the cavity wall of the installation cavity to jointly limit the assembly space for the installation of the refrigeration unit 60. The assembly space may be located directly above the thermal conductive portion 43, so that the refrigeration unit 60 is located directly above the thermal conductive portion 43, so that the heat transferred to the end cap 42 can be quickly absorbed by the refrigeration unit 60 and cool the end cap 42, which is conducive to speeding up the heat dissipation efficiency of the thermal conductive portion 43, thereby improving the heat dissipation efficiency of the first heat dissipation convex portion 720. In addition, the refrigeration unit 60 is provided at the assembly space, making full use of various areas of the installation cavity inside the handle 200, making the internal structure more compact and conducive to reducing the size of the handle 200.

Figure 20:
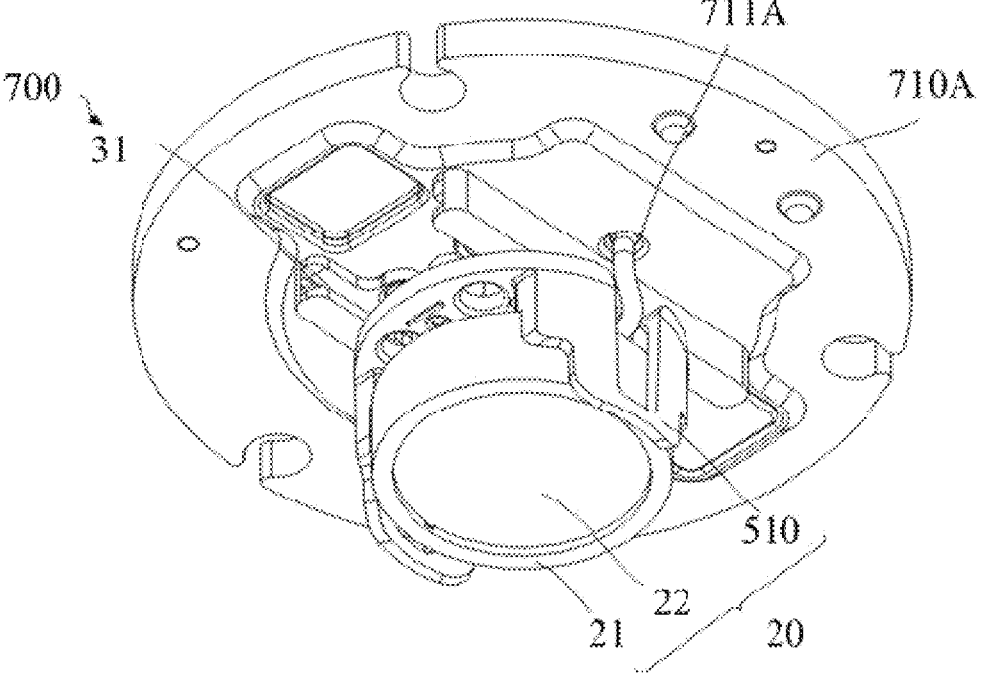
FIG. 20 is a structural schematic view of the heat dissipation structure and a transducer module.
Figure 21:
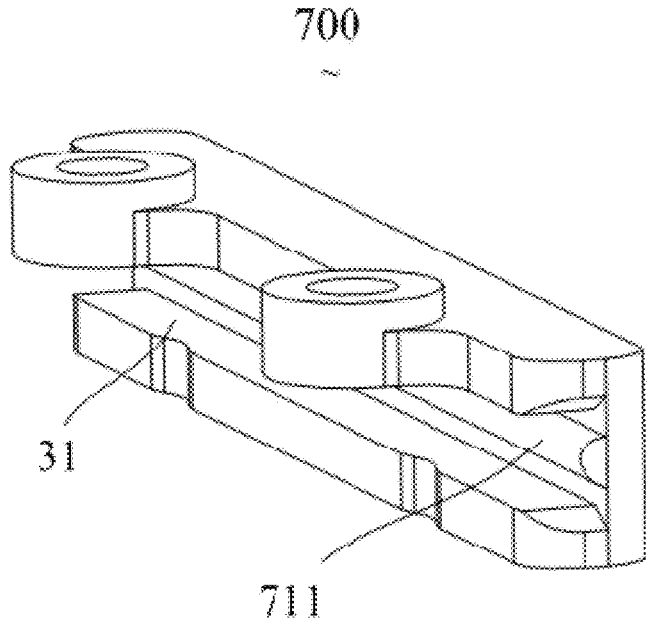
FIG. 21 is a structural schematic view of the guide rail.
Figure 22:
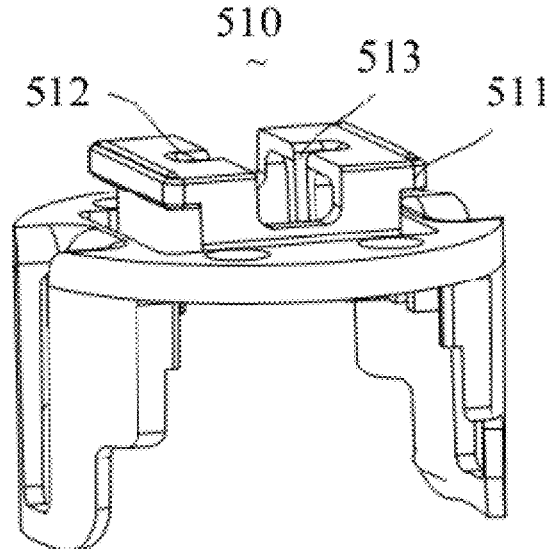
FIG. 22 is a structural schematic view of the transducer bracket.

Referring to FIG. 20 to FIG. 22, in an embodiment, a guide rail 700 is provided in the receiving cavity, the transducer module 20 includes a transducer bracket 510 slidingly cooperated with the guide rail 700, the transducer bracket 510 is provided with a push-against groove 512 for the second end 620 to extend into, the push-against groove 512 is provided with two opposite push-against surfaces 513 in the extension direction of the guide rail 700, and the second end 620 is configured to push against the push-against surface 513. Setting in this way, under the guidance function of the guide rail 700 and driven by the swing member 83, different push-against surfaces 513 are pushed against by the second end 620, so that the transducer module 20 reciprocates reliably and smoothly along the guide rail 700, which is conducive to obtaining more precise treatment at the treatment area.

The second end 620 can slide on the push-against surface 513, when the trajectory of the guide rail 700 is inconsistent with the trajectory of the first end 610, the swing of the transducer module 20 can be converted into a movement along the trajectory of the guide rail 700 by the sliding of the second end 620 on the push-against surface 513, which can effectively avoid interference between the linkage structure and the transducer module 20, for example, the trajectory of the guide rail 700 may be, but is not limited to, a straight line. Certainly, the present application is not limited to this, in other embodiments, the second end 620 is fixed at the transducer module 20.

Two guide rails 700 are provided, and the two guide rails 700 are both fixed on the shell 400, the two guide rails 700 are provided in parallel, and the transducer module 20 is slidably provided between the two guide rails 700. In this way, it further enables the transducer module 20 to slide on the guide rail 700 more smoothly, and also conducive to dispersing the force of the transducer module 20 acting on the guide rail 700. The guide rail 700 and the shell 400 can be connected and fixed by the means of bolting, snapping, embedding or the like.

Referring to FIG. 18, FIG. 28 and FIG. 29, in an embodiment, the linkage mechanism 90 includes a swing rod 630 rotatably passed through the center of the cover body 501 and a push rod 640 passed through the swing rod 630, one end of the swing rod 630 is drivingly connected to the transmission mechanism 600, another end of the swing rod 630 is for the push rod 640 to be rotatably passed through, the push rod 640 is configured to push against the push-against surface 513, and the push rod 640 and the push-against surface 513 are provided in parallel. It can be understood that, one end of the swing rod 630 is provided with the buffer drill way 92, and the swing member 83 is inserted into and slidably passed through the buffer drill way 92, so that the swing rod 630 can be driven by the swing member 83 to swing, thereby driving the push rod to swing.

The swing rod 630 is provided at the center of the cover body 501, which facilitates the swing rod 630 to drive the transducer module 20 to move, at the same time, the first heat dissipation convex portion 720 of the above-mentioned heat dissipation structure 420 extends via the avoidance opening 12 of the cover body 501, and the heat dissipation main body 710A is provided to be attached to the cover body 501, at this time, the cover body 501 is also provided with a through-hole corresponding to the circuit adapter board 17, so that the circuit adapter board 17 is electrically connected to the circuit board in the handle 200 via the through-hole. It can be understood that, for the normal working of the circuit adapter board 17, the through-hole and the avoidance opening 12 are respectively provided at the opposite sides of the swing rod 630.

Since the push rod 640 and the push-against surface 513 are provided in parallel, when the push rod 640 pushes against the push-against surface 513, the push rod 640 can roll relative to the push-against surface 513 to reduce the resistance between the push rod 640 and the push-against surface 513, so that the linkage mechanism 90 drives the transducer module 20 to reciprocate relatively smoothly. It can be understood that, in this embodiment, the push rod 640 is equivalent to the second end 620 mentioned above.

In an embodiment, a spherical pair structure 96 is provided between the linkage mechanism 90 and the cover body 501; that is, a spherical pair structure 96 is provided between the swing rod 630 and the cover body 501; specifically, the cover body 501 is provided with a connecting through-hole, and the hole wall of the connecting through-hole is provided with a first spherical arc surface, the swing rod 630 is provided with a second spherical arc surface that forms the spherical pair structure 96 with the spherical arc surface. It can be understood that, the spherical pair has a relatively high degree of freedom, making it difficult for the swing rod 630 and the cover body 501 to interfere during relative movement, at the same time, it is beneficial for the swing rod 630 to swing flexibly under the drive of the swing member 83, thereby meeting the movement requirements of the transducer module 20. In order to improve the sealing performance between the swing rod 630 and the cover body 501, a first sealing ring is provided between the swing rod 630 and the connecting through-hole, so that can improve the tightness of the receiving cavity and prevent the ultrasonic transmission medium from leaking out. In addition, the end cap 42 is provided with an avoidance groove avoiding the second spherical arc surface at the connection via hole for the swing member 83 to pass through, so as to facilitate the smooth swing of the swing rod 630, and it is also convenient to improve the connection tightness between the cover body 501 and the end cap 42 at the same time.

Referring to FIG. 21 and FIG. 22, in an embodiment, the guide rail 700 is provided with a guide chute 31, the transducer bracket 510 is provided with a sliding protrusion 511 slidingly cooperating with the guide chute 31, the groove bottom of the guide chute 31 is provided with a rib 711 for the sliding protrusion 511 to abut against, and the rib 711 extends along an extension direction of the guide chute 31. Setting in this way, by matching the sliding protrusion 511 with the rib 711, the effective contact area between the guide rail 700 and the transducer bracket 510 can be reduced, the resistance is reduced, thereby reducing the energy loss when the transducer module 20 slides at the guide rail 700, and improving the efficiency of the transmission.

Referring to FIG. 18 and FIG. 20, in an embodiment, the transducer module 20 further includes a transducer main body 21 provided at the transducer bracket 510, the transducer bracket 510 is fixed on the heat dissipation structure 420, and the sound-emitting surface 22 of the transducer main body 21 is a spherical structure or a tile surface structure. It can be understood that the transducer bracket 510 is connected to the heat dissipation main body 710A of the heat dissipation structure 420, on the one hand, it can fix the transducer main body 21, thereby preventing the transducer body 21 from shaking during use, and facilitating the installation and arrangement of the power supply cord and the assembly of the transducer module 20 to the treatment tip 100; on the other hand, it is also possible to reduce the temperature of the transducer bracket 510 and improve the use reliability of the transducer bracket 510 by heat exchange between the transducer bracket 510 and the heat dissipation main body 710A.

Figure 23:
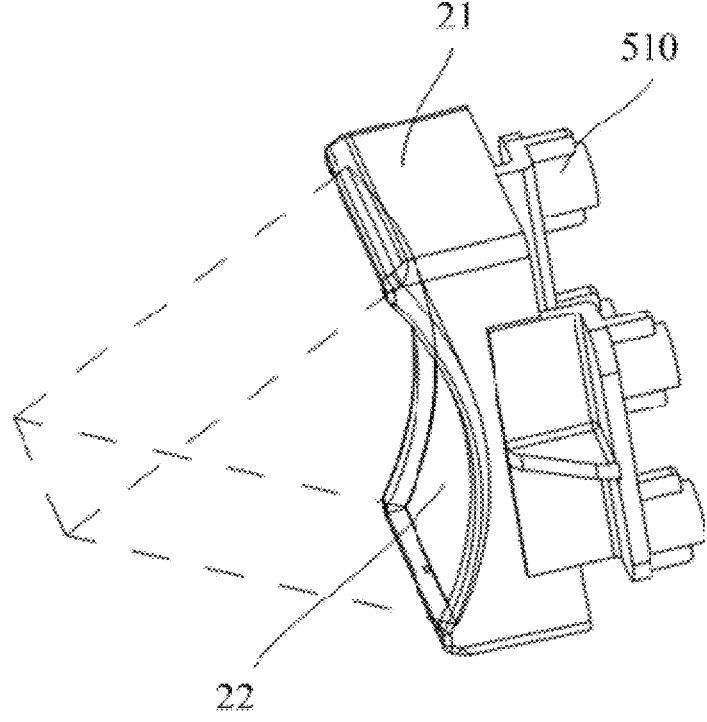
FIG. 23 is a structural schematic view of a main body of the transducer according to another embodiment.

In an embodiment, as shown in FIG. 20 and FIG. 28, the sound-emitting surface 22 of the transducer main body 21 is a spherical structure, at this time, the focusing area of the sound-emitting surface 22 is the spherical center position of the spherical structure, its emission area is large and the focusing gain is also large, which can greatly enhance the energy at the focus of the ultrasonic wave, thereby helping to accurately and efficiently act on the treatment area to achieve the purpose of treatment. In another embodiment, as shown in FIG. 23, the sound-emitting surface 22 is a tile surface structure, at this time, the ultrasonic waves emitted by the sound-emitting surface 22 intersect in their emission directions and are focused into a line shape, which is conducive to increasing the focusing area of the transducer module 20, and thereby shortening the treatment time.

The present application proposes an ultrasonic therapeutic apparatus.

Referring to FIG. 31 to FIG. 34, in the embodiment of the present application, the ultrasonic therapeutic apparatus includes a treatment tip 100, a handle 200 and a heat dissipation device. The handle 200 includes an outer shell 401 and an end cap 42, the outer shell 401 and the end cap 42 are connected to form an installation cavity, the treatment tip 100 is installed at the end cap 42, and the end cap 42 is provided with a thermal conductive portion 43; and the heat dissipation device includes a first heat dissipation module 30 and a second heat dissipation module 40, the first heat dissipation module 30 is provided at the treatment tip 100 and is thermally connected to the thermal conductive portion 43, the second heat dissipation module 40 is provided at the installation cavity and is thermally connected to the thermal conductive portion 43, and heat generated by the treatment tip 100 is transferred to the second heat dissipation module 40 via the first heat dissipation module 30 and the thermal conductive portion 43 in sequence. In this way, by the interaction between the thermal conductive portion 43 and the heat dissipation device, the heat generated in the treatment tip 100 can be dissipated, the heat dissipation efficiency is improved, the normal emission of ultrasonic waves in the treatment tip 100 and focusing on the treatment area of the patient are ensured, thereby achieving the purpose of treatment.

The thermal conductive portion 43 can be made of a material with the good thermal conductivity. The thermal conductive portion 43 can be a part of the end cap 42, or the whole can be the thermal conductive portion 43, so as to ensure efficient heat transfer performance of the thermal conductive portion 43 as an intermediate medium performing heat transfer between the first heat dissipation module 30 and the second heat dissipation module 40, thereby achieving the purpose of heat dissipation of the treatment tip 100.

The emission of ultrasonic waves in the treatment tip 100 is generally achieved by means of a device such as the transducer module 20. Since ultrasonic waves cannot pass through the air when they are transmitted to human tissue, a filling medium is provided between the sound-emitting surface 22 of the transducer module 20 and the human tissue, that is, a filling medium such as water, silicone oil, gel material and so on is provided inside the treatment tip 100, and the filling medium at least covers the sound-emitting surface 22 of the transducer module 20, so as to ensure normal propagation of ultrasonic waves.

The first heat dissipation module 30 is provided in the treatment tip 100 and is in contact with the filling medium, so that the heat generated when the transducer module 20 is working can be transferred to the first heat dissipation module 30 via the filling medium, and then transferred to the second heat dissipation module 40 via the thermal conductive portion 43. In this way, it can improve the heat dissipation efficiency of the treatment tip 100 and the use security of the ultrasonic therapeutic apparatus, prevent the heat generated by the transducer module 20 from causing thermal burns to the patient, and prolong the service life of the transducer module 20.

The second heat dissipation module 40 is provided inside the installation cavity of the handle 200 and is thermally connected to the thermal conductive portion 43. It can be understood that the second heat dissipation module 40 may be in direct contact with the thermal conductive portion 43, or may also be connected via a thermally conductive material such as thermally conductive silicone grease, and then, on the one hand, it can efficiently receive the heat transferred by the thermal conductive portion 43 and speed up the heat dissipation efficiency of the first heat dissipation module 30; on the other hand, the final heat is transferred to the installation cavity and can be discharged via the handle 200, thus avoiding heating the air around the treatment area and further improving the heat dissipation efficiency.

The outer shell 401 and the end cap 42 can be detachably connected to facilitate the formation of the installation cavity and the assembly of related components. The treatment Tip 100 can also be detachably connected to the end cap 42, which is conducive to the disassembly, maintenance and replacement, and improves the ease of use and assembly efficiency of the ultrasonic therapeutic apparatus.

The technical solution of the present application uses the interaction of the thermal conductive portion 43 and the heat dissipation device to dissipate the heat generated inside the treatment tip 100, improve the heat dissipation efficiency, and ensure that the ultrasonic waves inside the treatment tip 100 are normally emitted and focused on the treatment area of the patient, thereby achieving the purpose of treatment. The heat dissipation device includes the first heat dissipation module 30 and the second heat dissipation module 40; the first heat dissipation module 30 and the second heat dissipation module 40 are respectively provided at both sides of the thermal conductive portion 43, and are thermally connected to the thermal conductive portion 43, so as to ensure that the heat generated inside the treatment tip 100 is transferred to the second heat dissipation module 40 via the first heat dissipation module 30 and the thermal conductive portion 43 in sequence, and improve the heat dissipation efficiency of the treatment tip 100 and the use security of the ultrasonic therapeutic apparatus while accelerating the heat dissipation efficiency of the first heat dissipation module 30.

Figure 31:
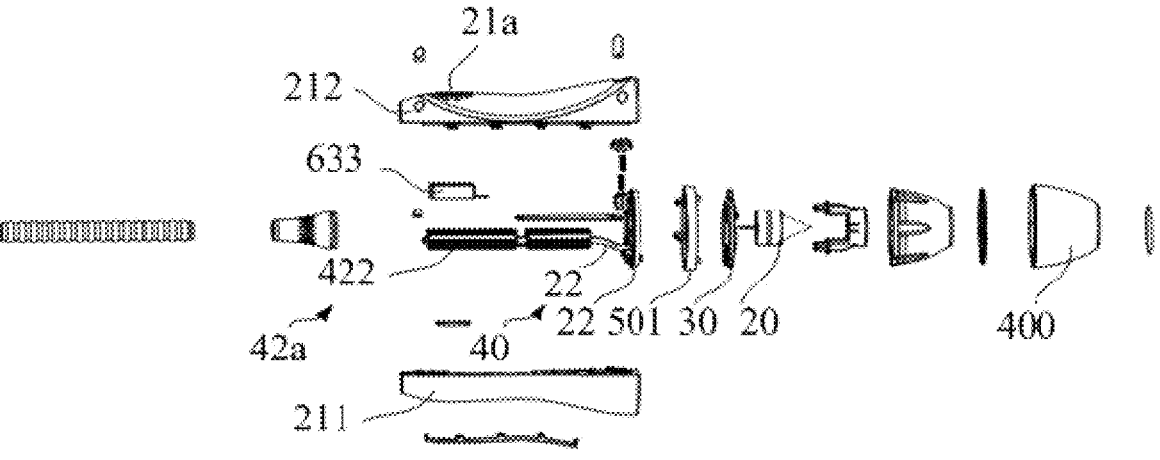
FIG. 31 is an exploded view of the ultrasonic therapeutic apparatus according to an embodiment of the present application.
Figure 32:
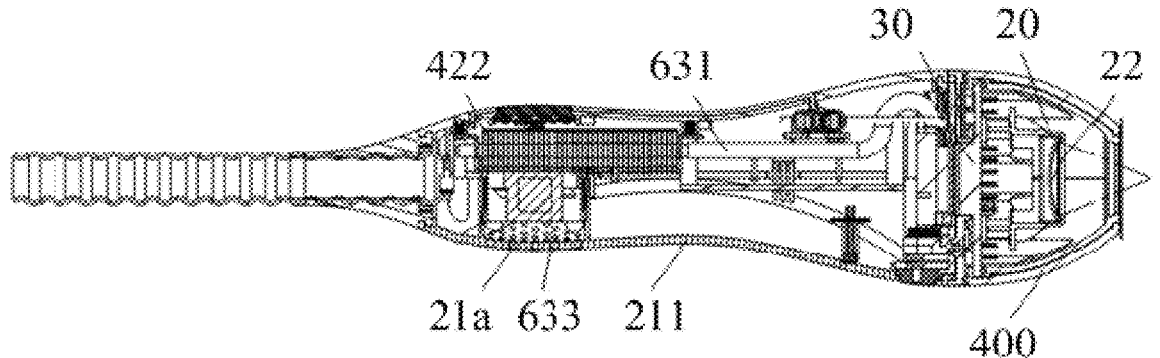
FIG. 32 is a section view of the ultrasonic therapeutic apparatus.
Figure 33:
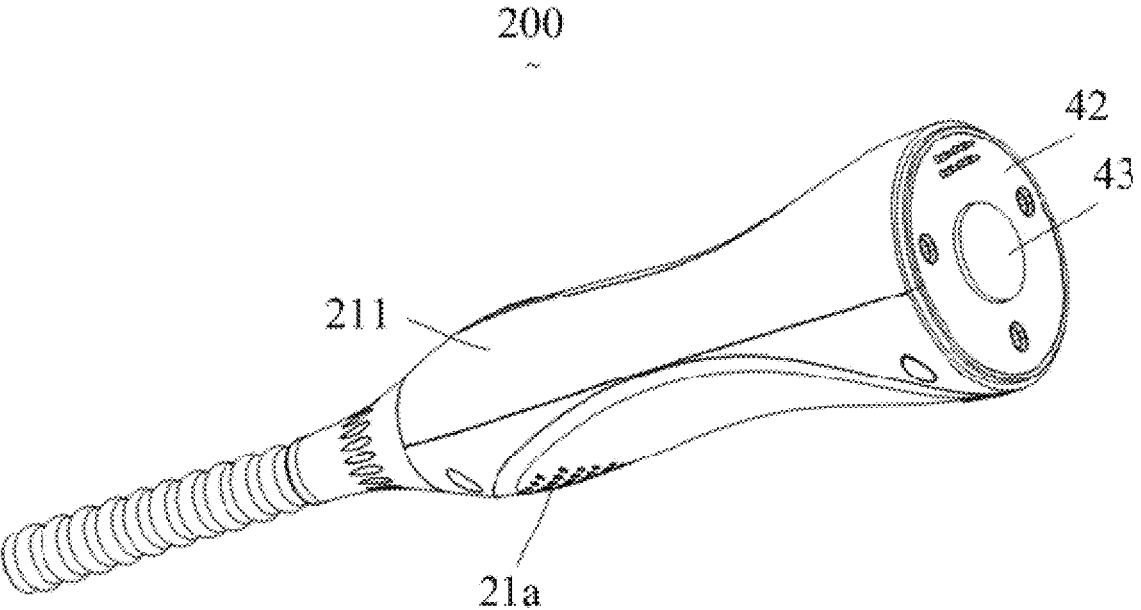
FIG. 33 is a structural schematic view of a handle.
Figure 34:
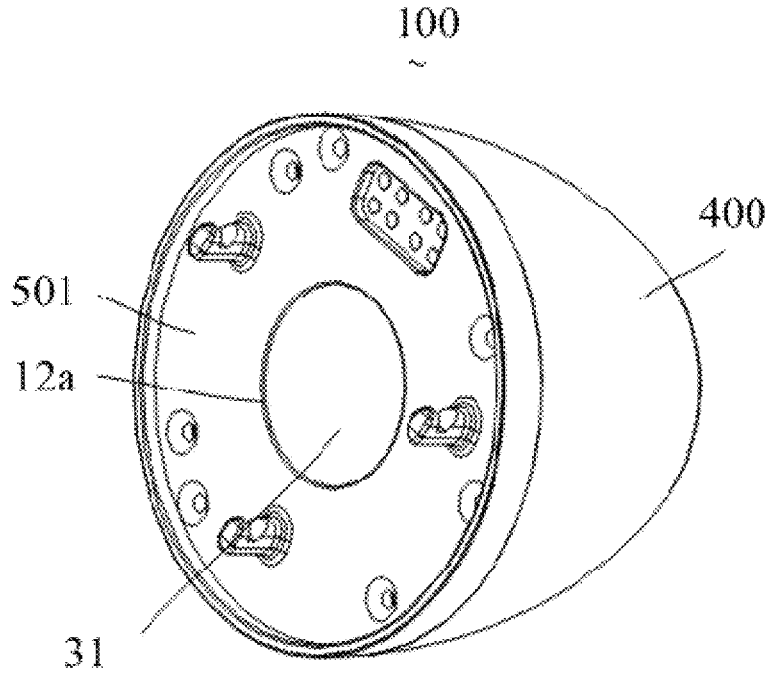
FIG. 34 is a structural schematic view of the treatment tip.

Referring to FIG. 31, FIG. 32 and FIG. 33, the treatment tip 100 includes a shell 400 and a cover body 501, and the shell 400 and the cover body 501 are connected to form a sealed accommodation cavity; and the first heat dissipation module 30 is fixedly provided at the cover body 501 and is at least partially exposed at the cover body 501 to abut against the thermal conductive portion 43. Setting in this way, while facilitating the quick assembly of the first heat dissipation module 30, the thermal conductivity efficiency between the thermal conductive portion 43 and the first heat dissipation module 30 is improved.

The shell 400 and the cover body 501 can be fixed to each other in a detachably connected manner such as buckles or the like to form a sealed accommodation cavity, so that the accommodation cavity is filled with filling medium, thus ensuring the normal propagation of ultrasonic waves and avoiding the leakage of the filling medium. The first heat dissipation module 30 is installed on the cover body 501 and is at least partially exposed at the cover body 501, it can be understood that the first heat dissipation module 30 may be an integral part of the cover body 501, or the first heat dissipation module 30 and the cover body 501 may be configured separately. Specifically, the first heat dissipation module 30 can protrude from the side of the cover body 501 facing the end cap 42, or can be provided flush with the surface of the cover body 501 facing the end cap 42, or can even be recessed on the surface of the cover body 501 facing the end cap 42, and it only needs to be thermally connected to the thermal conductive portion 43 to complete the heat transfer.

In an embodiment, the cover body 501 is provided with a through-hole 12*a*, a bump 31 is provided at one side of the first heat dissipation module 30 facing the handle 200, and the bump 31 is exposed at the through-hole 12*a*. Setting in this way is conducive to improving the assembly efficiency of the first heat dissipation module 30 and increasing the heat transfer effectiveness of the first heat dissipation module 30 and the thermal conductive portion 43.

By the precise alignment and assembly of the bump 31 and the through-hole 12*a*, on the one hand, it is conducive to improving the assembly precision and assembly efficiency of the first heat dissipation module 30 and the cover body 501; on the other hand, since the bump 31 is exposed at the through-hole 12*a*, that is, the bump 31 can protrude from the surface of the cover body 501 facing the end cap 42, it can be provided flush with the surface of the cover body 501 facing the end cap 42, or even recessed on the surface of the cover body 501 facing the end cap 42, so as to be thermally connected to the thermal conductive portion 43.

Specifically, referring to FIG. 33, in an embodiment, the thermal conductive portion 43 is protruding from one side of the end cap 42 facing the treatment tip 100. At this time, the bump 31 on the first heat dissipation module 30 is recessed on the surface of the cover body 501 facing the end cap 42, and then the thermal conductive portion 43 can insert into the through-hole 12*a* and abut against the bump 31, and then it can improve the heat transfer efficiency of the thermal conductive portion 43 and the first heat dissipation module 30 while playing a positioning role for the assembly of the handle 200 and the treatment tip 100. Certainly, the present application is not limited thereto, in other embodiments, the thermal conductive portion 43 may be provided flush with the side of the end cap 42 facing the treatment tip 100.

Referring to FIG. 31 and FIG. 32, in an embodiment, the second heat dissipation module 40 includes a heat pipe 631, and one end of the heat pipe 631 is fixedly connected to the thermal conductive portion 43. In this way, the heat dissipation efficiency of the thermal conductive portion 43 can be enhanced.

Specifically, the heat pipe 631 is provided with a heat-absorbing end and a heat dissipation end, the heat-absorbing end is fixedly connected to the thermal conductive portion 43. A connection hole can be opened in the thermal conductive portion 43, the heat-absorbing end can be inserted into the connection hole, thus, the outer wall of the heat-absorbing end can be closely attached to the hole wall of the connection hole, improving the heat conduction effect between the heat pipe 631 and the thermal conductive portion 43 while increasing the effective contact area between the heat pipe 631 and the thermal conductive portion 43, and then making the working medium in the heat-absorbing end evaporate into gas quickly and flow to the heat dissipation end, the gas condenses into liquid at the heat dissipation end and releases heat to the outside of the tube, thereby achieving the purpose of quickly reducing the temperature of the thermal conductive portion 43, prompting the first heat dissipation module 30 to be able to further absorb the heat inside the treatment tip 100 and transfer it to the thermal conductive portion 43, thus improving the heat dissipation efficiency of the treatment tip 100.

The pipe shell of the heat pipe 631 can be made of thermally conductive materials such as aluminum, copper or the like, thereby facilitating the heat pipe 631 to quickly transfer heat to the working medium inside the pipe. And the heat pipe 631 can be fixed on the cavity wall of the installation cavity by the mounting bracket.

In an embodiment, the second heat dissipation module 40 further includes a radiation fin group 42*a*, the radiation fin group 42*a* includes a plurality of radiation fins 422, and each of the radiation fins 422 is provided at intervals and is provided in series at one end of the heat pipe 631 away from the thermal conductive portion 43. It can be understood that a through hole 12*a* is provided in the middle area of the radiation fin 422, each radiation fin 422 is provided at intervals, and each through hole 12*a* can be provided to be connected, so that the heat dissipation end of the heat pipe 631 can pass through each through hole 12*a* in sequence, and the heat dissipation area is increased by the setting of the radiation fin 422, thereby enabling the heat at the heat dissipation end to be dissipated quickly and effectively and enhancing the heat dissipation efficiency of the heat pipe 631.

In addition, the heat dissipation through-hole 12*a* can be opened on the radiation fin 422, the setting of the heat dissipation through-hole 12*a* can further increase the heat dissipation area of the radiation fin 422, and it is conducive to further improving the heat dissipation efficiency of the heat pipe 631.

Specifically, in an embodiment, two radiation fin groups 42*a* are provided, and the two radiation fin groups 42*a* are provided in series at the heat pipe 631 at intervals. It is understandable that within the scope of space allowance and heat dissipation requirements, multiple groups of radiation fin groups 42*a* can be provided in series on the heat pipe 631 to increase the heat dissipation area and enhance the heat dissipation effect.

Referring to FIG. 31 and FIG. 32, in an embodiment, the second heat dissipation module 40 further includes a fan 633, and an air outlet of the fan 633 is provided facing the heat pipe 631. Setting in this way, the air outlet of the fan 633 is provided facing the heat dissipation end of the heat pipe 631, the pressure difference formed when the fan 633 is working can be utilized, and the external air flows into the installation cavity to form an air flow, so that the heat from the heat dissipation end of the heat pipe 631 is dissipated to the outside of the handle 200 along with the air flow to prevent hot air from gathering inside the handle 200 and affecting the normal use of other parts.

When the heat dissipation end of the heat pipe 631 is provided with a radiation fin group 42*a*, the air flow generated by the work of fan 633 can act on the radiation fin group 42*a*, that is, the airflow can flow through the side wall of the radiation fin 422, and can flow through the heat dissipation through-hole 12*a*, so that the heat on the radiation fin 422 can be efficiently and quickly dissipated to the outside of the handle 200 along with the airflow. Certainly, the number of fans 633 can be provided according to the radiation fin group 42*a*, that is, one fan 633 corresponds to one radiation fin group 42*a*, or one fan 633 corresponds to multiple radiation fin groups 42*a* to achieve heat dissipation requirements.

Referring to FIG. 31, in an embodiment, the outer shell 401 includes a first shell portion 211 and a second shell portion 212 detachably connected to the first shell portion 211, the heat pipe 631 is fixedly provided at the first shell portion 211, and the fan 633 is provided at the second shell portion 212. Setting in this way is beneficial to the maintenance and assembly of the handle 200, and is convenient for the air flow generated by the fan 633 when working to act on the heat pipe 631, thereby improving the heat dissipation effect of the heat pipe 631.

The outer shell 401 is provided with a heat dissipation hole 21*a*, so that hot air inside the outer shell 401 is discharged from the outer shell 401 via the heat dissipation hole 21*a*. The heat dissipation hole 21*a* is provided with a second shell portion 212 provided directly opposite the fan 633, so as to facilitate the entry and exit of external air and internal airflow, and speed up the discharge efficiency of hot air.

Referring to FIG. 31 and FIG. 32, in an embodiment, a transducer module 20 is provided inside the treatment tip 100, the transducer module 20 is provided with a sound-emitting surface 22, the sound-emitting surface 22 is a spherical structure. in this way, the focusing area of the sound-emitting surface 22 of the transducer module 20 is the spherical center position of the spherical structure, its emission area is large and the focusing gain is also large, which can greatly enhance the energy at the focus of the ultrasonic wave, thereby helping to accurately and efficiently act on the treatment area to achieve the purpose of treatment.

Figure 35:
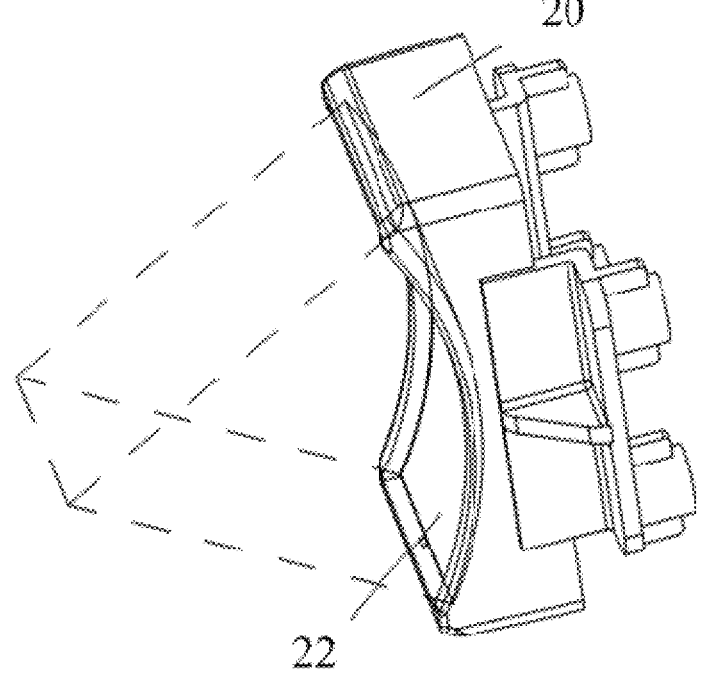
FIG. 35 is a structural schematic view of the transducer module according to another embodiment.

In another embodiment, as shown in FIG. 35, the sound-emitting surface 22 is a tile surface structure. At this time, the ultrasonic waves emitted by the sound-emitting surface 22 intersect in their emission directions and are focused into a line shape, which is conducive to increasing the focusing area of the transducer module 20, and thereby shortening the treatment time.

The present application further proposes an ultrasonic therapeutic apparatus 100. The ultrasonic therapeutic apparatus 100 includes an ultrasonic treatment handle 200 and the aforementioned ultrasonic treatment tip 300. The specific structure of the ultrasonic treatment tip 300 refers to the above-mentioned embodiments. Since the ultrasonic therapeutic apparatus 100 adopts all the technical solutions of all the above-mentioned embodiments, it has at least all the beneficial effects brought by the technical solutions of the above embodiments, which will not be described again one by one here. The cover body 501 of the ultrasonic treatment tip 300 is connected to the ultrasonic treatment handle 200.

The above are only some embodiments of the present application, and are not intended to limit the scope of the present application. Under the concept of the present application, any equivalent structure transformation made by utilizing the description and accompanying drawings of the present application, or directly or indirectly applied in other related technical fields, is included within the scope of the present application.

What is claimed is:

1. An ultrasonic treatment tip, comprising:
a shell provided with a receiving cavity, wherein the shell is provided with a heat dissipation structure;
a transducer module provided at the receiving cavity;
wherein the heat dissipation structure is configured to dissipate heat from the transducer module to outside of the ultrasonic treatment tip; and
the ultrasonic treatment tip further comprises:
a cover body covering a first port, wherein the cover body and an outer shell are configured to limit an installation cavity, the cover body is provided with an avoidance hole connected to the installation cavity, and the cover body is connected to an ultrasonic treatment handle;
the heat dissipation structure further comprises a heat dissipation main body provided at a second port and a first heat dissipation convex portion passed through the avoidance hole, wherein the first heat dissipation convex portion is connected to the heat dissipation main body;
a sound-permeable membrane, wherein the ultrasonic treatment tip is provided with a sound-permeable opening passed through the outer shell and an inner shell, and the sound-permeable membrane is provided at the sound-permeable opening;

a transducer provided with a vibrating sound-emitting surface provided toward the sound-permeable membrane; and
the shell comprises the outer shell provided with the first port and the inner shell provided at the installation cavity, the inner shell is provided with the receiving cavity for receiving an ultrasonic transmission medium, and the receiving cavity is provided with the second port.

2. The ultrasonic treatment tip according to claim 1, wherein the heat dissipation structure further comprises at least one second heat dissipation convex portion provided at the receiving cavity.

3. The ultrasonic treatment tip according to claim 2, further comprising:
the ultrasonic transmission medium received at the receiving cavity;
wherein the second heat dissipation convex portion is immersed into the ultrasonic transmission medium.

4. The ultrasonic treatment tip according to claim 2, wherein a plurality of the second heat dissipation convex portions are provided, including the at least one second heat dissipation convex portion.

5. The ultrasonic treatment tip according to claim 1, wherein the heat dissipation main body is configured to cover the second port, the heat dissipation main body is provided with a wire via hole for a wire harness of the transducer to pass through, and the ultrasonic treatment tip further comprises a first plugging element provided between the wire via hole and the wire harness of the transducer; and/or
the heat dissipation main body is provided with a via hole for the ultrasonic transmission medium, and the ultrasonic treatment tip further comprises a second plugging element provided at the via hole for the ultrasonic transmission medium.

6. The ultrasonic treatment tip according to claim 1, wherein the heat dissipation main body is provided with an avoidance area, the cover body is provided with a wire via hole for a wire harness of the transducer to pass through, the ultrasonic treatment tip further comprises a first plugging element provided between the wire via hole and the wire harness of the transducer, and the wire via hole is exposed at the avoidance area; and/or
the cover body is provided with a via hole for the ultrasonic transmission medium, the ultrasonic treatment tip further comprises a second plugging element provided at the via hole for the ultrasonic transmission medium, and the via hole for the ultrasonic transmission medium is exposed at the avoidance area.

7. The ultrasonic treatment tip according to claim 1, further comprising:
a transducer bracket provided at the heat dissipation main body, wherein the transducer is provided at the transducer bracket; and/or
a sealing ring is provided between the inner shell and the heat dissipation main body.

8. The ultrasonic treatment tip according to claim 1, further comprising:
a transmission mechanism rotatably passing through the shell, wherein the transmission mechanism is provided with a first end and a second end, the first end is transmission connected to the transducer module, the second end is configured to drivingly connected to a driving member, and the transmission mechanism is configured to drive the transducer module to perform reciprocating motion.

9. The ultrasonic treatment tip according to claim 8, wherein the shell comprises a shell body provided with the first port and the heat dissipation structure covering the first port, the shell body and the heat dissipation structure are configured to limit the receiving cavity, and the transmission mechanism is passed through the heat dissipation structure.

10. The ultrasonic treatment tip according to claim 8, wherein the heat dissipation structure is provided with an installation hole connected to the receiving cavity, and the ultrasonic treatment tip further comprises a buffer film assembly provided at the installation hole.

* * * * *